United States Patent
Watanabe

(10) Patent No.: US 10,590,443 B2
(45) Date of Patent: *Mar. 17, 2020

(54) METHOD FOR PRODUCING MULTIPLE OIL/FAT COMPOSITIONS BY COMPLEX TRANSESTERIFICATION REACTION SYSTEM

(71) Applicant: FUJI OIL HOLDINGS INC., Osaka (JP)

(72) Inventor: Shimpei Watanabe, Kaizuka (JP)

(73) Assignee: FUJI OIL HOLDINGS INC., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/077,761

(22) PCT Filed: Feb. 23, 2016

(86) PCT No.: PCT/JP2016/055253
§ 371 (c)(1),
(2) Date: Aug. 14, 2018

(87) PCT Pub. No.: WO2017/141448
PCT Pub. Date: Aug. 24, 2017

(65) Prior Publication Data
US 2019/0048370 A1 Feb. 14, 2019

(30) Foreign Application Priority Data
Feb. 19, 2016 (JP) ................................ 2016-029423

(51) Int. Cl.
*C12P 7/64* (2006.01)
*C11C 3/10* (2006.01)

(52) U.S. Cl.
CPC .............. *C12P 7/6454* (2013.01); *C11C 3/10* (2013.01); *C12Y 301/01003* (2013.01)

(58) Field of Classification Search
CPC ... C11C 3/10; C12Y 301/01003; C12P 7/6454
See application file for complete search history.

(56) References Cited

U.S. PATENT DOCUMENTS

| 4,876,107 A | 10/1989 | King et al. |
| 4,877,636 A | 10/1989 | Koyano et al. |
| 4,910,037 A | 3/1990 | Sagi et al. |
| 5,023,101 A | 6/1991 | Sugihara et al. |
| 5,508,048 A * | 4/1996 | Padley ...................... A23D 9/00 426/33 |
| 5,849,939 A | 12/1998 | Mittelbach et al. |
| 6,361,980 B2 * | 3/2002 | Sugiura ................. C12P 7/6454 435/134 |
| 8,153,407 B2 | 4/2012 | Schweitzer et al. |
| 8,183,021 B2 | 5/2012 | Cain et al. |
| 8,496,986 B2 * | 7/2013 | Sagi .......................... A23D 9/04 426/601 |
| RE44,719 E | 1/2014 | Schweitzer et al. |
| 10,385,369 B2 * | 8/2019 | Watanabe ................. C11C 3/10 |
| 2009/0104673 A1 | 4/2009 | Cain et al. |
| 2009/0130728 A1 | 5/2009 | Schweitzer et al. |
| 2017/0267945 A1 | 9/2017 | Schweitzer et al. |

FOREIGN PATENT DOCUMENTS

| JP | 62-25936 | 2/1987 | |
| JP | 63-240745 | 10/1988 | |
| JP | 64-60330 | 3/1989 | |
| JP | 2-406 | 1/1990 | |
| JP | 4-135453 | 5/1992 | |
| JP | 9-500155 | 1/1997 | |
| JP | 2002-65162 | 3/2002 | |
| JP | 2003-81915 | 3/2003 | |
| JP | 2007-176973 | * 7/2007 | ................ C10L 1/02 |
| JP | 2009-507479 | 2/2009 | |
| WO | 2007/029018 | 3/2007 | |
| WO | 2008/104381 | 9/2008 | |

OTHER PUBLICATIONS

International Search Report dated May 31, 2016 in International (PCT) Application No. PCT/JP2016/055253.
International Preliminary Report on Patentability dated Aug. 21, 2018 in International (PCT) Application No. PCT/JP2016/055253.

* cited by examiner

*Primary Examiner* — Ganapathirama Raghu
(74) *Attorney, Agent, or Firm* — Wenderoth, Lind & Ponack, L.L.P.

(57) ABSTRACT

The present invention addresses the problem of providing a method for effectively producing a target oil/fat that is rich in triglyceride, by using liberated by-products such as fatty acid ester originating from starting material oil/fat that is separated from the target oil/fat efficiently after the reaction when producing the target oil/fat that is rich in triglyceride by a transesterification reaction using, for example, oil/fat and fatty acid ester as starting materials.

21 Claims, 3 Drawing Sheets

[Fig. 1]
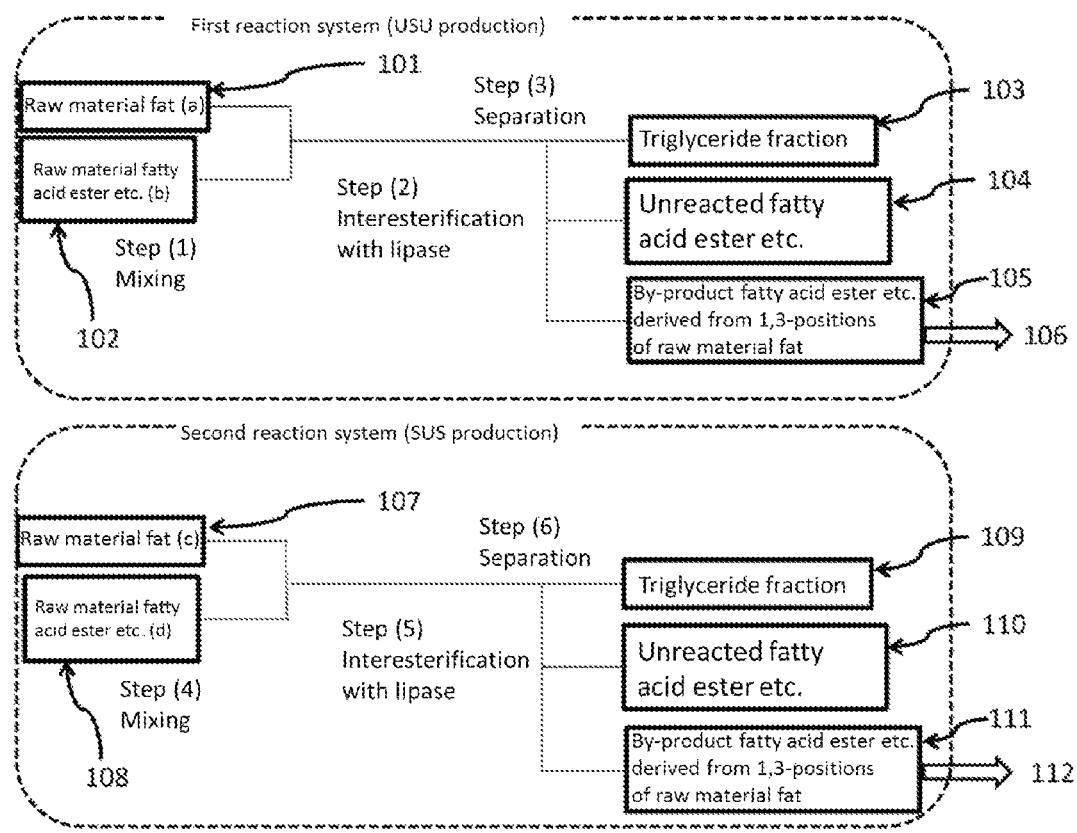

[Fig. 2]
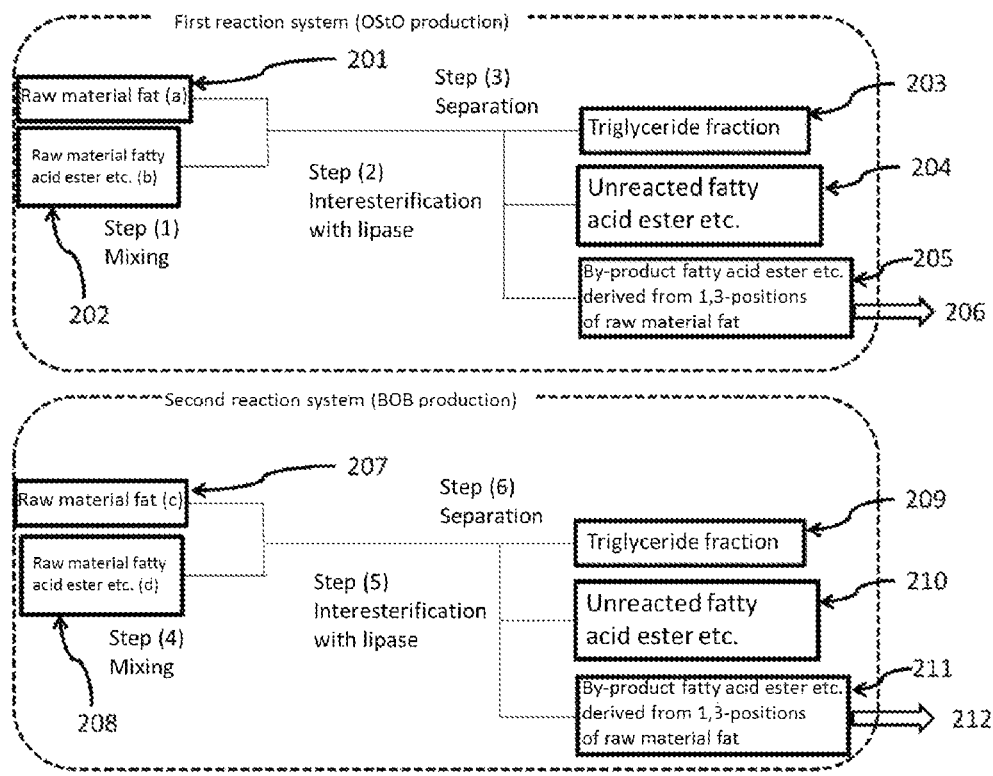
[Fig. 3]
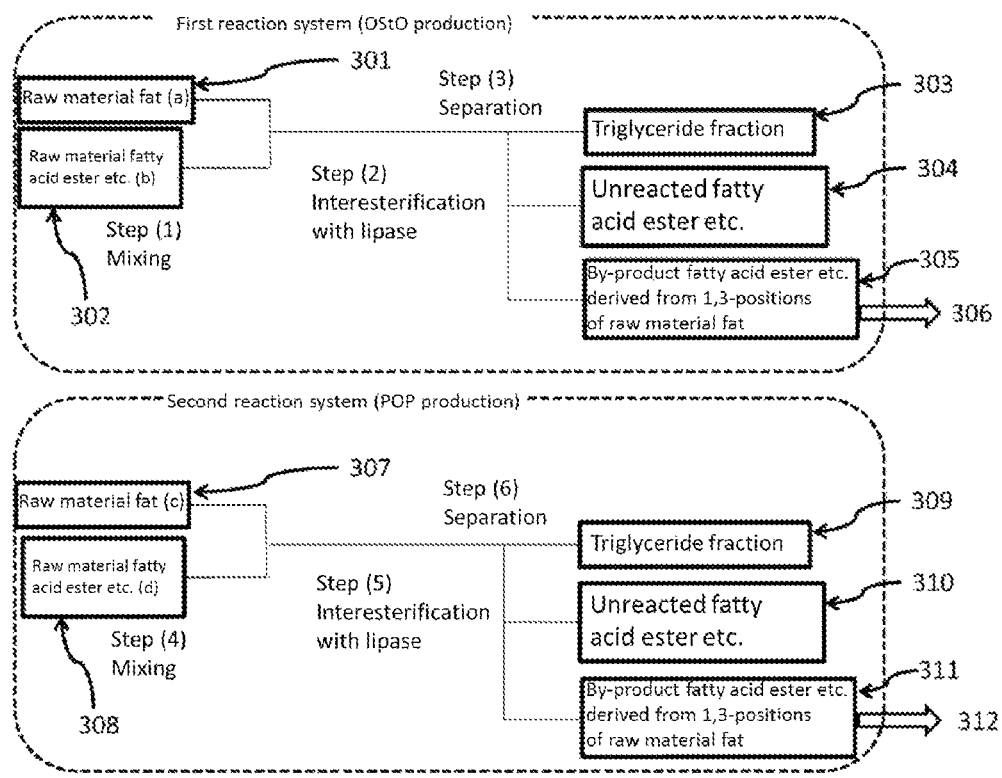

[Fig. 4]
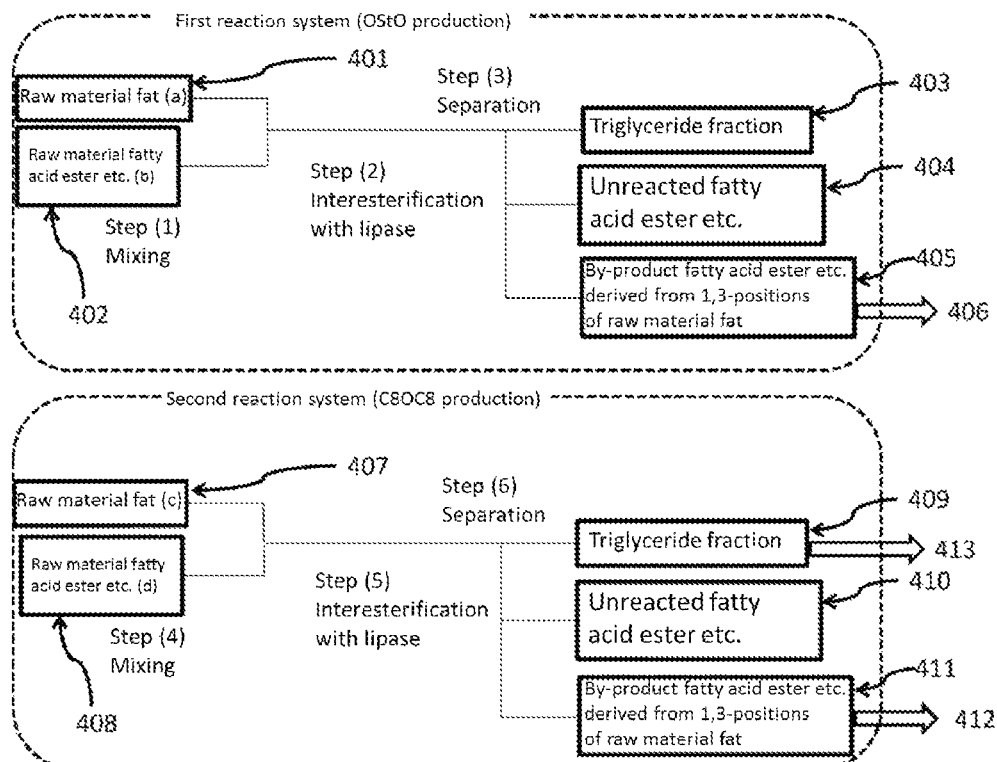
[Fig. 5]
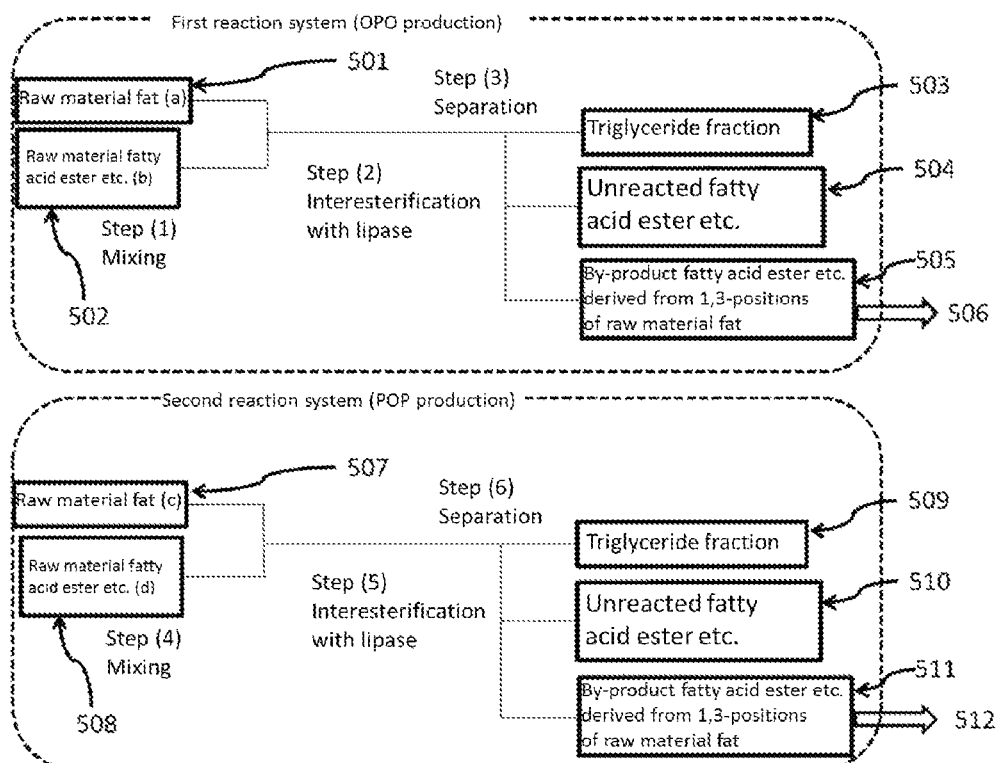

METHOD FOR PRODUCING MULTIPLE OIL/FAT COMPOSITIONS BY COMPLEX TRANSESTERIFICATION REACTION SYSTEM

TECHNICAL FIELD

The present invention relates to a process for producing a plurality of fats by a combined interesterification reaction system which effectively utilizes by-products mutually.

BACKGROUND ART

A triglyceride composition is converted by enzyme interesterification of fat with fatty acid or lower alcohol ester thereof (hereinafter, referred to as "fatty acid ester etc.") to increase purity of a specific triglyceride molecular species and thus to modify properties of the fat. However, this reaction is an equilibrium reaction, and therefore, when a target triglyceride purity is higher, a larger amount of an expensive raw material fatty acid ester etc. is required to be used, resulting in high cost.

In particular, high-purity USU fat and SUS fat (U: C18 unsaturated fatty acid, S: C4 to C24 saturated fatty acids) which are produced by interesterification with enzymes are highly demanded from the market, and inexpensive production process has been desired. However, use thereof in the market has not progressed due to high price due to the above reason.

As a fat rich in USU, for example, Patent Document 1 discloses a cocoa butter equivalent containing 40 to 100% by weight of mixed acid group triglyceride in which a saturated fatty acid with C16 to C22 is bound to a glycerin at 2-position and an unsaturated fatty acid with C16 to C18 and one unsaturated bond is bound to the glycerin at 1,3-positions as constituent fatty acids.

Patent Document 1 discloses that this mixed acid group triglyceride USU exhibits the following peculiar physical properties. The mixed acid group triglyceride USU forms a peculiar crystalline structure with mixed acid group triglyceride SUS, which is the main component of a cocoa butter. By combining the mixed acid group triglyceride USU as a raw material of a chocolate, a bloom is not observed at all without performing a tempering. The obtained chocolate shows that resistivity of a crystal against a pressure is significantly small although it shows a melting point almost same as that of ordinary chocolates.

As an example of a process for producing OStO (where St is stearic acid and O is oleic acid), which is one kind of the mixed acid group triglyceride, Example 1 of Patent Document 2 discloses a method including interesterification of fully hydrogenated soybean oil and ethyl oleate using 1,3-position-selective enzyme, molecular distillation, fractionation, and refining. However, ethyl oleate used for the production of OStO fat is relatively expensive, and there is a problem that if a high purity product is to be obtained, the production cost is high.

As a fat rich in SUS, for example, Patent Documents 3 to 5 disclose that powder particles mainly composed of BOB (B is behenic acid and O is oleic acid) are added to a chocolate compound without being dissolved, so that occurrence of a bloom is significantly suppressed, and in addition, tempering operation can be omitted. Thus, the fat rich in SUS is peculiar and useful fat material for the chocolate industry. However, behenic acid used for the production of BOB fat is still relatively expensive and has a problem of high production cost as described above.

As a fat rich in USU, for example, Patent Document 6 discloses a technique of using fat rich in OPO as a milk fat substitute composition, and Patent Documents 7 and 8 propose a process for producing a fat rich in OPO. However, there is no description concerning the collection and use of relatively expensive oleic acid used as a raw material, and it could not be said to be an efficient OPO fat production process.

Patent Document 9 discloses a production process in which a fat by-produced in the production of StOSt fat is hydrolyzed and then the resulting product is used for a fatty acid raw material for OPO fat production. However, there is no disclosure concerning effective utilization of components by-produced in the production of the OPO, and it could not be said to be an efficient OPO fat production process.

PRIOR ART DOCUMENTS

Patent Documents

Patent Document 1: JP H4-135453 A
Patent Document 2: JP 2002-65162 A
Patent Document 3: JP S63-240745 A
Patent Document 4: JP S64-60330 A
Patent Document 5: JP H2-406 A
Patent Document 6: JP S62-025936 A
Patent Document 7: WO 2008/104381
Patent Document 8: WO 2007/029018
Patent Document 9: JP 2009-507479 A

SUMMARY OF INVENTION

Problems to be Solved by Invention

When a fat rich in triglyceride is produced by interesterification using fat, fatty acid ester etc. as raw materials, a fatty acid ester etc. separated from the target fat after the reaction become a mixture of the fatty acid ester etc. liberated and by-produced derived from the raw material fat (the fatty acid ester etc. is hereinafter referred to as "by-product fatty acid ester etc.") and an unreacted raw material fatty acid ester etc. (hereinafter referred to as "unreacted fatty acid ester etc."). When the mixture is reused as it is as a raw material fatty acid ester etc. for the next reaction, the purity is often insufficient, and even if the mixture can be reused while the purity is increased by suitable separation means, there has been no means to effectively utilize the by-product fatty acid ester etc. produced simultaneously by the separation. Thus, in the prior art, the by-product fatty acid ester etc. is discarded or used for a low-value-added product, and it results high cost of production of target fat. An object of the present invention is to provide a process for easily producing a fat containing a specific triglyceride with high purity at a low cost and relates particularly to a process for easily producing a fat rich in USU and a fat rich in SUS at a low cost at a commercially available level. Here, S represents a saturated fatty acid with C4 to C24, and U represents an unsaturated fatty acid with C18.

Means for Solving Problems

The inventor has extensively studied for solving the above problems. As a result, the inventor has found that in a plurality of reaction systems, there is provided a combined reaction system in which a plurality of reaction systems using by-product fatty acid ester etc. as raw material fatty acid ester etc. in another reaction system are combined, so that fatty acid ester etc. which have been discarded or used for a low-value-added product may be effectively utilized, and the production cost may be significantly reduced. The present invention has been completed based on these findings.

Further, the inventor has completed a novel process for producing a fat containing USU and a fat containing SUS according to the basic invention described above. That is, in a first reaction system which produces a fat composition rich in USU and a second reaction system which produces a fat composition rich in SUS, by virtue of a combined reaction system in which fatty acid ester etc. of S by-produced derived from raw material fat in the first reaction system is used for raw material fatty acid ester etc. of S in the second reaction system, and fatty acid ester etc. of U by-produced derived from raw material fat in the second reaction system is used for raw material fatty acid ester etc. of U in the first reaction system, the above problem may be solved at once.

That is, the first aspect of the present invention is a process for producing a plurality of fat compositions by a combined reaction system, where the combined reaction system includes a plurality of reaction systems which produce a target fat composition rich in triglyceride by 1,3-position specific interesterification of raw material fat and raw material fatty acid or lower alcohol ester thereof, including:

separating a fraction of fatty acid or lower alcohol ester thereof, which is liberated derived from 1,3-positions of the raw material fat, from a reaction product after the 1,3-position specific interesterification in each of the reaction systems; and using the fraction as a part or all of raw material fatty acid or lower alcohol ester thereof in another reaction system.

The second aspect of the present invention is the process for producing a plurality of fat compositions according to the first aspect, where the combined reaction system includes a first reaction system which produces a fat composition rich in USU and a second reaction system which produces a fat composition rich in SUS, the first reaction system includes the following steps (1) to (3), the second reaction system includes the following steps (4) to (6), where a fraction obtained in step (6) is used for a part or all of raw material fatty acid or lower alcohol ester thereof (b) in step (1), and where a fraction obtained in step (3) is used for a part or all of raw material fatty acid or lower alcohol ester thereof (d) in step (4),
where S represents saturated fatty acid with C4 to C24, U represents unsaturated fatty acid with C18, USU represents triglyceride in which fatty acids at 1,3-positions are U and fatty acid at 2-position is S, and SUS represents triglyceride in which fatty acids at 1,3-positions are S and fatty acid at 2-position is U, and where steps (1) to (6) are as follows:

(1) a step of mixing raw material fat (a) containing 80% by weight or more of S in the constituent fatty acid and raw material fatty acid or lower alcohol ester thereof (b) containing U as a major component;

(2) a step of subjecting the raw material mixture obtained in step (1) to interesterification using 1,3-position-specific lipase;

(3) a step of separating a fraction of fatty acid or lower alcohol ester thereof, which is liberated derived from the 1,3-positions of the raw material fat (a), from a reaction product obtained in step (2);

(4) a step of mixing raw material fat (c) containing 50% by weight or more of U in the constituent fatty acid and raw material fatty acid or lower alcohol ester thereof (d) containing S as a major component;

(5) a step of subjecting the raw material mixture obtained in step (4) to interesterification using 1,3-position-specific lipase; and (6) a step of separating a fraction of fatty acid or a lower alcohol ester thereof, which is liberated derived from the 1,3-positions of the raw material fat (c), from a reaction product obtained in step (5).

The third aspect of the present invention is the process for producing a plurality of fat compositions according to the second aspect, where in step (3), a fat composition containing 30% by weight or more of USU and a fraction of unreacted fatty acid or lower alcohol ester thereof are separated from the reaction product.

The fourth aspect of the present invention is the process for producing a plurality of fat compositions according to the second or third aspect, where in step (6), a fat composition containing 30% by weight or more of SUS and a fraction of unreacted fatty acid or a lower alcohol ester thereof are separated from the reaction product.

The fifth aspect of the present invention is the process for producing a plurality of fat compositions according to any one of the second to fourth aspects, where a distillation method is used for a part or all of the separation in step (3) or step (6).

The sixth aspect of the present invention is the process for producing a plurality of fat compositions according to any one of the second to fifth aspects, where the USU contains stearic acid (St) as a major component of fatty acid at 2-position, and has 0.5 or more of UStU/USU ratio.

The seventh aspect of the present invention is the process for producing a plurality of fat compositions according to the sixth aspect, where the raw material fat (a) contains 10 to 70% by weight of saturated fatty acid with C20 to C24 in the constituent fatty acid.

The eighth aspect of the present invention is the process for producing a plurality of fat compositions according to the seventh aspect, where a fully hydrogenated oil of high erucic rapeseed oil is used for a part or all of the raw material fat (a), oleic acid or lower alcohol ester thereof is used for the raw material fatty acid or lower alcohol ester thereof (b), high oleic fat is used for a part or all of the raw material fat (c), and behenic acid or lower alcohol ester thereof is used for the raw material fatty acid or lower alcohol ester thereof (d).

The ninth aspect of the present invention is the process for producing a plurality of fat compositions according to the sixth aspect, where the raw material fat (a) contains 10 to 70% by weight of saturated fatty acid with C4 to C16 in the constituent fatty acid.

The tenth aspect of the present invention is the process for producing a plurality of fat compositions according to the ninth aspect, where a fully hydrogenated oil of palm mid fraction is used for a part or all of the raw material fat (a), oleic acid or lower alcohol ester thereof is used for the raw material fatty acid or lower alcohol ester thereof (b), high oleic fat is used for a part or all of the raw material fat (c), and palmitic acid or lower alcohol ester thereof is used for the raw material fatty acid or lower alcohol ester thereof (d).

The eleventh aspect of the present invention is the process for producing a plurality of fat compositions according to the ninth aspect, where the raw material fat (a) is a fat rich in saturated fatty acid with C4 to C14 at 1,3-positions and rich in stearic acid at 2-position, oleic acid or lower alcohol ester thereof is used for the raw material fatty acid or lower alcohol ester thereof (b), high oleic fat is used for a part or all of the raw material fat (c), and saturated fatty acid with C4 to C14 or lower alcohol ester thereof is used for the raw material fatty acid or lower alcohol ester thereof (d).

The twelfth aspect of the present invention is the process for producing a plurality of fat compositions according to any one of the sixth to eleventh aspects, where a triglyceride fraction obtained in step (6) is fully hydrogenated and used for a part or all of the raw material fat (a) in step (1).

The thirteenth aspect of the present invention is the process for producing a plurality of fat compositions according to any one of the second to fifth aspects, where the USU contains palmitic acid (P) as a major component of fatty acid at 2-position, and has 0.5 or more of UPU/USU ratio.

The fourteenth aspect of the present invention is the process for producing a plurality of fat compositions according to the thirteenth aspect, where the raw material fat (a) contains 60% by weight or more of palmitic acid in the constituent fatty acid.

The fifteenth aspect of the present invention is the process for producing a plurality of fat compositions according to the fourteenth aspect, where a fat rich in tripalmitin is used for a part or all of the raw material fat (a), oleic acid or lower alcohol ester thereof is used for the raw material fatty acid or lower alcohol ester thereof (b), high oleic fat is used for a part or all of the raw material fat (c), and palmitic acid or lower alcohol ester thereof is used for the raw material fatty acid or lower alcohol ester thereof (d).

Effects of Invention

The present invention enables to effectively utilize by-product fatty acid ester etc., which have been discarded or used for a low-value-added product and to significantly reduce production cost of target fat, in addition, it enables to produce a target fat rich in triglyceride in which no waste is generated or waste is significantly reduced, which are environmentally friendly. The production cost may be further significantly reduced by circularly using fractionated by-product fat for a raw material fat and circularly using a fraction of unreacted fatty acid etc. for raw material fatty acid ester etc. in each reaction system. According to the first to third aspects to be described later, SUS fat obtained in a second reaction system is hydrogenated and thereafter used for a raw material fat in a first reaction system, whereby UStU-containing fat may be produced using only high oleic fat as a raw material such that by-product is not produced or is reduced.

BRIEF DESCRIPTION OF DRAWINGS

FIG. 1 is a conceptual diagram of a USU-SUS combined reaction system which is one aspect of the present invention.

FIG. 2 is a conceptual diagram of Example 1 which is an example of Aspect 1 of the present invention.

FIG. 3 is a conceptual diagram of Example 2 which is an example of Aspect 2 of the present invention.

FIG. 4 is a conceptual diagram of Example 3 which is an example of Aspect 3 of the present invention.

FIG. 5 is a conceptual diagram of Example 4 which is an example of Aspect 4 of the present invention.

MODE FOR CARRYING OUT INVENTION

Hereinafter, the present invention will be described in detail.

The definitions of the terms used in the present invention will be described. In the present invention, fatty acid ester etc. refers to a fatty acid or lower alcohol ester thereof. An interesterification system or reaction system refers to a series of steps in which raw material fat and raw material fatty acid ester etc. are subjected to 1,3-position specific interesterification and a target fat composition and fatty acid ester etc. are separated from a reaction product. A combined interesterification system or a combined reaction system refers to a combined system which mutually exchanges by-products in a plurality of reaction systems.

The present invention provides a process for producing a plurality of fat compositions by a combined reaction system, where in a combined reaction system including a plurality of reaction systems, a fraction of by-product fatty acid ester etc. is separated from a reaction product after 1,3-position specific interesterification in each of the reaction systems, and the fraction is used as a part or all of raw material fatty acid ester etc. in another reaction system. The number of the reaction systems included in the combined reaction system is not particularly limited. The combined reaction system includes preferably two or three, more preferably two reaction systems. For example, in the combined reaction system including two reaction systems, two types of fat compositions are produced by using fatty acid ester etc., by-produced in the first reaction system, for a raw material in the second reaction system and using fatty acid ester etc., by-produced in the second reaction system, for a raw material in the first reaction system. For example, in the combined reaction system including three reaction systems, three types of fat compositions are produced by using a first by-product for a second raw material, using a second by-product for a third raw material, and using a third by-product for a first raw material.

The types of raw material fat and raw material fatty acid ester etc. in each reaction system are not particularly limited, but are subject to certain restrictions. That is, it is necessary to select a combination of raw materials such that fatty acid ester etc. mutually exchanged in the combined reaction system are the same type of fatty acid as raw material fatty acid ester etc. in the reaction system as an exchange destination. When distillation is used for separating fractions of fatty acid ester etc. after interesterification, it is necessary to select a combination of raw materials such that by-product fatty acid ester etc. mutually exchanged have a sufficient boiling point difference.

There are no particular restrictions other than the above constraints, and various raw materials may be used. Specific examples of a fat include vegetable oil such as sunflower oil, high oleic sunflower oil, safflower oil, high oleic safflower oil, soybean oil, rapeseed oil, olive oil, palm oil, sal fat, Shea butter, coconut oil, and palm kernel oil, animal oil such as fish oil, beef tallow, and lard, synthetic triglyceride such as MCT and trilaurin, one or more mixed oils selected from structure lipid etc. in which one or more mixed oils selected from structure lipid etc. in which specific fatty acids are bonded to the 1,3-positions and the 2-position, respectively, and processed fat obtained therefrom (including one or more processing steps selected from hydrogenation, fractionation, and interesterification), and examples of fatty acid ester etc. include fatty acid with C4 to C24 such as butyric acid, caproic acid, caprylic acid, capric acid, lauric acid, myristic acid, palmitic acid, stearic acid, oleic acid, linoleic acid, linolenic acid, behenic acid, DHA, and EPA and ester of lower alcohol such as methyl or ethyl ester thereof.

A lipase produced by microorganism such as genus *Rhizopus*, genus *Aspergillus*, and genus *Mucor* may be used in the 1,3-position specific interesterification according to the present invention. Any lipases other than the above-described lipases may be used as long as the lipases have a similar property to these lipases. Such lipase is commercially available, and for example, Amano A (Amano Enzyme Inc.), and Lipozyme (Novo Nordisk Pharma Ltd.) may be used. The type of usage of the lipase is not particularly limited, and the lipase is preferably used with immobilized to a carrier by a known method from a viewpoint of efficiency. Additionally, a chemically modified enzyme is preferably used under an organic solvent. This reaction may be performed by a batch method using a stir tank or a continuation method using a filled reactor.

A raw material mixture subjected to enzyme interesterification in the present invention is preferably bleached and deodorized by a known method before the reaction in order to suppress reduction in enzyme activation as much as possible. A water content in the raw material mixture is desired to be adjusted low in order to reduce a hydrolysis reaction as much as possible to reduce generation of diglyceride, but it is desired to be adjusted high in order to enhance a reaction rate. The water content is desired to be adjusted to 10 to 300 ppm, preferably 20 to 200 ppm, and more preferably 30 to 100 ppm. A period of the enzyme reaction is not particularly limited as long as a sufficient interesterification rate is achieved, and is preferably two hours to four days. A temperature of the enzyme reaction is desirable to be 30 to 90° C., more preferably 35 to 75° C., and further preferably 40 to 55° C. from the viewpoints of maintaining enzyme activation long while securing the sufficient enzyme reaction rate and reducing generation of isomer triglyceride as much as possible.

In the present invention, a fraction of the by-product fatty acid ester etc. derived from the 1,3-positions of the raw material fat is separated from a reaction product after 1,3-position specific interesterification in each reaction system, and the fraction is used as a part or all of raw material fatty acid ester etc. in another reaction system as it is or after the purity of target fatty acid ester etc. is increased by a known method such as distillation, fractionation, or adsorption. When the fraction of the by-product fatty acid ester etc. derived from the 1,3-positions of the raw material fat is separated from the reaction product, the fraction may be separated into at least three fractions including a triglyceride fraction and a fraction of unreacted fatty acid ester etc. And, the triglyceride fraction among them is a fat composition rich in target specific triglyceride. The fraction of unreacted fatty acid ester etc. may be circularly used as a part or all of raw material fatty acid ester etc. in the same reaction system. In some cases, separation between the triglyceride fraction and the fraction of unreacted fatty acid ester etc. is not performed, 1,3-position specific interesterification is performed with or without further adding thereto a fatty acid ester etc. of the same type as unreacted fatty acid ester etc., and then the triglyceride fraction is separated, so that a target fat composition having an improved specific triglyceride purity may be obtained.

The separation into three fractions from the reaction product according to the present invention may be performed by a known separation method such as fractionation or distillation alone or by combining plural methods. Specific examples of the fractionation method include fractionation using a solvent, dry fractionation without solvent, and fractionation by a urea addition method. Specific examples of the distillation method include single distillation, steam distillation, thin film distillation, molecular distillation, and rectification distillation, so-called rectification. The distillation method is desirable from the viewpoint that easy, efficient, and more precise separation as separating means is possible.

Although the order of separation from the reaction product according to the present invention into the three fractions is not particularly limited, when the separation is performed by distillation, preferably, first distillation is first performed in which a triglyceride fraction and a fraction of fatty acid ester etc. having a large boiling point difference are distilled and separated, and second distillation is performed in which the latter fraction is further distilled and separated into a fraction of by-product fatty acid ester etc. derived from the 1,3-positions of the raw material fat and a fraction of unreacted fatty acid ester etc. having a relatively small boiling point difference. Rectification is suitably used for the second distillation. However, depending on convenience of the separation step, the fraction of by-product fatty acid ester etc. derived from the 1,3-positions of the raw material fat or the fraction of unreacted fatty acid ester etc. may be distilled and separated first, or the three fractions described above may be separated simultaneously.

When separation from the reaction product according to the present invention into the three fractions is performed by distillation, the conditions of the first and second distillations are appropriately selected according to the composition of the fatty acid ester etc. and the composition of the triglyceride fraction to be separated.

One aspect of the present invention is a combined reaction system including a first reaction system which produces a fat composition rich in USU and a second reaction system which produces a fat composition rich in SUS. (Hereinafter, this combined reaction system is referred to as the "USU-SUS combined reaction system". The conceptual diagram is shown in FIG. 1.) In the first reaction system, a fat rich in SSS (raw material fat (a)) and fatty acid ester etc. (raw material fatty acid ester etc. (b)) containing U as a major component are used for raw materials, and USU-containing fat is produced. In the second reaction system, a fat rich in UUU (raw material fat (c)) and fatty acid ester etc. (raw material fatty acid ester etc. (d)) containing S as a major component are used for raw materials, and SUS-containing fat is produced. At this time, by-product fatty acid ester etc., which is produced in the first reaction system, containing S, derived from the 1,3-positions of (a), as a major component is used as raw material fatty acid ester etc. (d) in the second reaction system, and by-product fatty acid ester etc., which is produced in the second reaction system, containing U, derived from the 1,3-positions of (c), as a major component is used as raw material fatty acid ester etc. (b) in the first reaction system.

In the USU-SUS combined reaction system, in step (1) of the first reaction system, the raw material fat (a) and the raw material fatty acid ester etc. (b) are mixed. The raw material fat (a) rich in SSS (see FIG. 1-101) is required to contain 80% by weight or more of S in the constituent fatty acid. And, the raw material fat (a) preferably contains 90% by weight or more, more preferably 95% by weight or more, and further preferably 98% by weight or more of S. When the S in the constituent fatty acid of the raw material fat (a) according to the present invention is less than 80% by weight, this triglyceride content in the fat composition containing USU may be reduced, and thus it is not preferable.

The raw material fatty acid ester etc. (b) containing U as a major component (see FIG. 1-102) preferably contains 80% by weight or more of U. And, the raw material fatty acid ester etc. (b) more preferably contains 90% by weight or more, further preferably 95% by weight or more, and most preferably 99% by weight or more of U.

In the USU-SUS combined reaction system, in step (4) of the second reaction system, the raw material fat (c) and the raw material fatty acid ester etc. (d) are mixed. The raw material fat (c) rich in UUU (see FIG. 1-107) is not particularly limited as long as U in the constituent fatty acid is 50% by weight or more, and the U in the constituent fatty acid is preferably 70% by weight or more, more preferably 80% by weight or more, and further preferably 90% by weight or more.

The raw material fatty acid ester etc. (d) containing S as a major component (see FIG. 1-108) preferably contains 80% by weight or more of S. And, the raw material fatty acid ester etc. (d) more preferably contains 90% by weight or more, further preferably 95% by weight or more, and most preferably 99% by weight or more of S.

In step (1) or step (4), a raw material other than the raw material fat (a) and the raw material fatty acid ester etc. (b) and a raw material other than the raw material fat (c) and the raw material fatty acid ester etc. (d) may be added unless the effects of the present invention are not degraded. A total amount of (a) and (b) or (c) and (d) in the raw material mixture is preferably 80% by weight or more, more preferably 90% by weight or more, further preferably 95% by weight or more, and most preferably 98% by weight or more.

In each 1,3-position specific interesterification in the USU-SUS combined reaction system, it is necessary to use a reaction temperature at which no crystal precipitation occurs during the reaction. When a continuation method using a filled reactor is applied to the interesterification, such a consideration is particularly important in order to avoid an obstruction inside the reactor. For example, in the case of the USU-SUS combined reaction system, in the first reaction system, the crystal precipitation temperature varies depending on a mixing ratio of the raw material fat (a) containing saturated fatty acid, which has a comparatively high-melting point, as a major component to the raw material fatty acid ester etc. (b) containing unsaturated fatty acid, which has a low-melting point, as a major component.

Thus, the mixing ratio in step (1) is advantageous when the raw material fatty acid ester etc. (b) is larger, and thus, the ratio of the raw material fatty acid ester etc. (b) in the raw material mixture is preferably 35% by weight or more, more preferably 50% by weight or more, and further preferably 60% by weight or more. In addition, the small amount of the raw material fat (a) reduces a production amount of fat composition as a triglyceride fraction obtained in step (3), resulting in the deterioration of production efficiency. From this point, the ratio of the raw material fat (a) in the raw material mixture is preferably 5% by weight or more, more preferably 10% by weight or more, and further preferably 20% by weight or more.

In addition, in the case of the USU-SUS combined reaction system, in the second reaction system, the crystal precipitation temperature varies depending on a mixing ratio of the raw material fat (c) containing unsaturated fatty acid, which has a comparatively low-melting point, as a major component to the raw material fatty acid ester etc. (d) containing saturated fatty acid, which has a comparatively high-melting point, as a major component.

Thus, the mixing ratio in step (4) is advantageous when the raw material fat (c) is larger, and thus, the ratio of the raw material fat (c) in the raw material mixture is preferably 10% by weight or more, more preferably 20% by weight or more, and further preferably 25% by weight or more. In addition, the small amount of the raw material fatty acid ester etc. (d) reduces a SUS content of a triglyceride fraction obtained in step (6), resulting in the deterioration of production efficiency. From this point, the ratio of the raw material fatty acid ester etc. (d) in the raw material mixture is preferably 20% by weight or more, more preferably 40% by weight or more, and further preferably 60% by weight or more.

In the case of the USU-SUS combined reaction system, in step (3) of the first reaction system or step (6) of the second reaction system, as a fraction of by-product fatty acid ester etc. derived from the 1,3-positions of the raw material fat, fatty acid ester etc. containing S as a major component (see FIG. 1-105) or fatty acid ester etc. containing U as a major component (see FIG. 1-111) is sequentially separated, and sequentially used as a part or all of the raw material fatty acid ester etc. (d) in step (4) of the second reaction system or the raw material fatty acid ester etc. (b) in step (1) of the first reaction system (see FIG. 1-106 or FIG. 1-112). When separation into at least three fractions including a triglyceride fraction and a fraction of unreacted fatty acid ester etc. is performed, the fraction of the unreacted fatty acid ester etc. (see FIG. 1-104 or FIG. 1-110) may be sequentially circularly reused for the raw material fatty acid ester etc. (b) in step (1) of the first reaction system or the raw material fatty acid ester etc. (d) in step (4) of the second reaction system.

In the USU-SUS combined reaction system, when the separation into three fractions in step (3) or (6) is performed by distillation, the temperature of the first distillation in which a triglyceride fraction and a fraction of fatty acid ester etc. are separated is preferably 180° C. or more, more preferably 200° C. or more, further preferably 210° C. or more, and most preferably 220° C. or more. In addition, the temperature of the first distillation is preferably 280° C. or less, more preferably 270° C. or less, and further preferably 260° C. or less. The degree of vacuum is preferably 0.2 torr or more, more preferably 0.5 torr or more, and further preferably 1 torr or more. In addition, the degree of vacuum is preferably 10 torr or less, more preferably 7 torr or less, further preferably 5 torr or less, and the most preferably 3 torr or less.

In addition, the conditions of the second distillation in which the fraction of by-product fatty acid ester etc. derived from the 1,3-positions of the raw material fat and the fraction of unreacted fatty acid ester etc. are separated and rectification are appropriately selected based on the composition of fatty acid ester etc. to be separated.

In the USU-SUS combined reaction system, a triglyceride fraction (see FIG. 1-103) obtained in step (3) of the first reaction system is a fat composition containing 30% by weight or more of USU.

The USU content may be increased by increasing the mixing ratio of raw material fatty acid ester etc. in step (1) or increasing the interesterification rate in step (2), and the USU content is preferably 40% by weight or more, more preferably 50% by weight or more, and most preferably 60% by weight or more.

In the USU-SUS combined reaction system, a triglyceride fraction (see FIG. 1-109) obtained in step (6) of the second reaction is a fat composition containing 30% by weight or more of SUS.

The SUS content may be increased by increasing the mixing ratio of raw material fatty acid ester etc. in step (4) or increasing the interesterification rate in step (5), and the SUS content is preferably 40% by weight or more, more preferably 50% by weight or more, and most preferably 60% by weight or more.

In the USU-SUS combined reaction system, when a USU-containing fat produced in the first reaction system is a fat rich in UStU (St is stearic acid), a UStU/USU ratio is preferably 0.5 or more, more preferably 0.7 or more, and further preferably 0.9 or more. One aspect (hereinafter referred to as the "Aspect 1") in this case is a process for producing a fat rich in OStO by using as the raw material fat (a) in the first reaction system fat which is rich in saturated fatty acid with C20 to C24 at the 1,3-positions and is rich in stearic acid at the 2-position and using oleic acid for the raw material fatty acid ester etc. (b) and for producing a fat rich in triglyceride which contains saturated fatty acid with C20 to C24 at the 1,3-positions and oleic acid at the 2-position, which is typified by BOB (B represents behenic acid) by using high oleic fat for the raw material fat (c) in the second reaction system and using saturated fatty acid with C20 to C24 for the raw material fatty acid ester etc. (d). Saturated fatty acid ester etc. with C20 to C24 derived from the 1,3-positions of the (a) by-produced in the first reaction system is used for the raw material fatty acid ester etc. (d) in the second reaction system, and oleate etc. derived from the 1,3-positions of the (c) by-produced in the second reaction system is used for the raw material fatty acid ester etc. (b) in the first reaction system. The conceptual diagram of Example 1 as an example of the Aspect 1 is shown in FIG. 2.

In the Aspect 1, it is preferable that saturated fatty acid with C20 to C24 in the constituent fatty acid of the raw material fat (a) is contained in an amount of 10 to 70% by weight, and the lower limit thereof is more preferably 20% by weight or more, further preferably 30% by weight or more, and most preferably 40% by weight or more. The upper limit of saturated fatty acid with C20 to C24 is more preferably 60% by weight or less, and further preferably 55% by weight or less. When saturated fatty acid with C20 to C24 in the constituent fatty acid of the raw material fat (a) is contained in an amount of less than 10% by weight, the amount of saturated fatty acid with C20 to C24 as by-product is reduced, and there is a problem that a sufficient amount may not be supplied as raw material fatty acid ester etc. in the second reaction system. When the content of saturated fatty acid with C20 to C24 exceeds 70% by weight, the content of St relatively decreases, so that a sufficient level of OStO fat production efficiency may not be obtained.

In the Aspect 1, the raw material fat (a) is preferably a fat which contains saturated fatty acid with C20 to C24 much at the 1,3-positions and little at the 2-position.

In this case, preferably 80% by weight or more, more preferably 90% by weight or more, further preferably 95% by weight or more, most preferably 98 weight % or more of saturated fatty acid with C20 to C24 in the constituent fatty acid of the raw material fat (a) are present at the 1,3-positions.

Further, in the Aspect 1, a content ratio of saturated fatty acid with C20 to C24 to the S content is preferably 0.2 or more, more preferably 0.3 or more, further preferably 0.4 or more, and preferably 0.85 or less, more preferably 0.75 or less, and further preferably 0.65 or less, in the constituent fatty acid of the raw material fat (a). When this content ratio is less than the lower limit, the amount of by-produced saturated fatty acid ester etc. with C20 to C24 is small, and there is a problem that a sufficient amount may not be supplied as raw material fatty acid ester etc. in the second reaction system. When the content ratio exceeds the upper limit, the content of St relatively decreases, so that a sufficient level of OStO fat production efficiency may not be obtained.

In the Aspect 1, the raw material fat (a) is not particularly limited as long as the above-described requirements for the fatty acid composition are met. Examples of the raw material fat (a) include fully hydrogenated oil such as fully hydrogenated high-erucic rapeseed oil, fully hydrogenated fish oil, and fully hydrogenated jojoba oil, and interesterified oil or fractionated oil in which one or more of the above described oils are used as a raw material. The raw material fat (a) is most preferably the fully hydrogenated high-erucic rapeseed oil.

In the Aspect 1, oleic acid or lower alcohol ester thereof is used for the raw material fatty acid ester etc. (b) in the first reaction system, and in particular ethyl oleate is preferable. The content of oleic acid is preferably 70% by weight or more, more preferably 75% by weight or more.

In the Aspect 1, a high oleic fat is used for the raw material fat (c) in the second reaction system, and the content of oleic acid with respect to total fatty acid is preferably 70% by weight or more, more preferably 80% by weight or more, further preferably 90% by weight or more, and the content of linoleic acid with respect to total fatty acid is 20% by weight or less, preferably 15% by weight or less, more preferably 10% by weight or less, and most preferably 7% by weight or less. Examples of fat used for the raw material fat (c) include high oleic sunflower oil, high oleic safflower oil, high oleic rapeseed oil, olive oil, interesterified oil and fractionated oil of one or more fats selected therefrom, and fats which abundantly contain oleic acid and are subjected to interesterification with oleic acid or oleate to introduce oleic acid into triglyceride and thus to increase its content.

In the Aspect 1, although saturated fatty acid ester etc. with C20 to C24 is used for the raw material fatty acid ester etc. (d) in the second reaction system, behenic acid is particularly preferably contained, and the content of behenic acid in the raw material fatty acid ester etc. (d) is preferably 60% by weight or more, more preferably 70% by weight or more, further preferably 80% by weight or more, and most preferably 90% by weight or more.

In the Aspect 1, in the second distillation in step (3) or (6), saturated fatty acid ester etc. with C20 to C24 and oleate etc. are separated.

The distillation temperature in this case is preferably 170° C. or more, more preferably 190° C. or more, further preferably 200° C. or more, and most preferably 210° C. or more. In addition, the distillation temperature is preferably 270° C. or less, more preferably 260° C. or less, and further preferably 250° C. or less. The degree of vacuum is preferably 0.2 torr or more, more preferably 0.5 torr or more, and further preferably 1 torr or more. In addition, the degree of vacuum is preferably 10 torr or less, more preferably 7 torr or less, further preferably 5 torr or less, and the most preferably 3 torr or less.

By the distillation, saturated fatty acid ester etc. with C20 to C24 is recovered to high-boiling point fraction, and oleate etc. is recovered to low-boiling point fraction.

In the Aspect 1, a fat rich in OStO is obtained in the first reaction system. In this case, the content of OStO is 30% by weight or more, preferably 40% by weight or more, more preferably 50% by weight or more, and most preferably 60% by weight or more. When fractionation is further performed, it is possible to obtain a fat composition having an improved OStO content in a fractionated low-melting point fraction, and a by-produced fractionated high-melting point fraction may be circularly reused as a portion of the raw material fat (a) in step (1).

In the Aspect 1, a fat rich in BOB is produced in the second reaction system. In this case, the content of BOB is 30% by weight or more, preferably 40% by weight or more, more preferably 50% by weight or more, and most preferably 60% by weight or more. When fractionation is further performed, it is possible to obtain a fat composition having an improved BOB content in a fractionated high-melting point fraction, and a by-produced fractionated low-melting point fraction may be circularly reused as a portion of the raw material fat (c) in step (4).

In the Aspect 1, the following advantageous effects are obtained. That is, a difference in boiling point between saturated fatty acid ester etc. with C20 to C24 and oleate etc. in the second distillation in step (3) or (6) is sufficiently large, and distillation separation is very effective. When a fat rich in OStO and a fat rich in BOB are fractionated, not only a high purity fat composition may be obtained, but also the production cost may be further reduced by circularly reuse of each fractionated by-product to a raw material fat. In addition, when a fraction of unreacted fatty acid etc. obtained in each reaction system is circularly reused for raw material fatty acid ester etc. in the reaction system, the production cost may be further reduced.

In the USU-SUS combined reaction system, another aspect (hereinafter referred to as the "Aspect 2") in the case where a USU-containing fat produced in the first reaction system is a fat rich in UStU (St is stearic acid) is a process for producing a fat rich in OStO by using a fat which is rich in palmitic acid at the 1,3-positions and is rich in stearic acid at the 2-position as the raw material fat (a) in the first reaction system and by using oleate etc. for the raw material fatty acid ester etc. (b) and for producing a fat rich in POP (P represents palmitic acid) by using high oleic fat for the raw material fat (c) in the second reaction system and using palmitate etc. for the raw material fatty acid ester etc. (d). Palmitate etc. by-produced in the first reaction system is used for the raw material fatty acid ester etc. (d) in the second reaction system, and oleate etc. by-produced in the second reaction system is used for the raw material fatty acid ester etc. (b) in the first reaction system. The conceptual diagram of Example 2 as an example of the Aspect 2 is shown in FIG. 3.

The raw material fat (a) in the Aspect 2 preferably contains palmitic acid in an amount of 10 to 70% by weight, and the lower limit thereof is more preferably 20% by weight or more, further preferably 30% by weight or more, and most preferably 40% by weight or more. The upper limit of palmitic acid is more preferably 60% by weight or less, and further preferably 55% by weight or less.

When palmitic acid in the constituent fatty acid of the raw material fat (a) according to the present invention is contained in an amount of less than 10% by weight, the amount of palmitate etc. as by-product is small, and there is a problem that a sufficient amount may not be supplied as raw material fatty acid ester etc. in the second reaction system. When the palmitic acid exceeds 70% by weight, the content of St relatively decreases, so that a sufficient level of UStU fat production efficiency may not be obtained.

In the Aspect 2, the raw material fat (a) is preferably fat which contains palmitic acid much at the 1,3-positions and does not contain palmitic acid at the 2-position in large amount.

In this case, preferably 80% by weight or more, more preferably 90% by weight or more, further preferably 95% by weight or more, most preferably 98% by weight or more of palmitic acid in the constituent fatty acid of the raw material fat (a) are present at the 1,3-positions. When such a raw material fat is used, it is possible to easily perform separation by distillation by utilizing a difference between respective boiling points of palmitate etc. by-produced after interesterification and unreacted oleate etc. Palmitate etc. concentrated by separation may be effectively used as raw material fatty acid ester etc. in the second reaction system.

In the Aspect 2, a content ratio of palmitic acid to the S content is preferably 0.2 or more, more preferably 0.3 or more, further preferably 0.4 or more, and preferably 0.85 or less, more preferably 0.75 or less, and further preferably 0.85 or less, in the constituent fatty acid of the raw material fat (a). When this content ratio is less than the lower limit, the amount of by-produced palmitate etc. is small, and there is a problem that a sufficient amount cannot be supplied as raw material fatty acid ester etc. in the second reaction system. When the content ratio exceeds the upper limit, the content of St relatively decreases, so that a sufficient level of UStU fat production efficiency may not be obtained.

In the Aspect 2, the raw material fat (a) is not particularly limited as long as the above-described requirements for the fatty acid composition are met. Examples of the raw material fat (a) include fully hydrogenated oil of palm mid fraction, and fully hydrogenated Chinese tallow oil, and interesterified oil or fractionated oil in which one or more of the above described oils are used as a raw material. The raw material fat (a) is most preferably the fully hydrogenated oil of palm mid fraction.

In the Aspect 2, details of oleate etc. of the raw material fatty acid ester etc. (b) and high oleic fat of the raw material fat (c) are the same as those of the first aspect.

In the Aspect 2, palmitate etc. is used for the raw material fatty acid ester etc. (d) in the second reaction system, and the content of palmitic acid in the (d) is preferably 60% by weight or more, more preferably 70% by weight or more, further preferably 80% by weight or more, and most preferably 90% by weight or more.

In the Aspect 2, in the second distillation in step (3) or (6), palmitate etc. and oleate etc. are separated. The distillation temperature in this case is preferably 120° C. or more, more preferably 140° C. or more, further preferably 150° C. or more, and most preferably 160° C. or more. In addition, the distillation temperature is preferably 220° C. or less, more preferably 210° C. or less, and further preferably 200° C. or less. The degree of vacuum is preferably 0.2 torr or more, more preferably 0.5 torr or more, and further preferably 1 torr or more. In addition, the degree of vacuum is preferably 10 torr or less, more preferably 7 torr or less, further preferably 5 torr or less, and the most preferably 3 torr or less.

By the distillation, palmitate etc. is recovered to low-boiling point fraction, and oleate etc. is recovered to high-boiling point fraction.

In the Aspect 2, a fat rich in OStO is obtained in the first reaction system as in the Aspect 1, and details thereof are the same as those in the Aspect 1.

In the Aspect 2, a fat rich in POP is produced in the second reaction system. In this case, the content of POP is 30% by weight or more, preferably 40% by weight or more, more preferably 50% by weight or more, and most preferably 60% by weight or more. When fractionation is further performed, it is possible to obtain a fat composition having an improved POP content in a fractionated high-melting point fraction, and a by-produced fractionated low-melting point fraction may be circularly reused as a portion of the raw material fat (c) in step (4).

In the Aspect 2, the following advantageous effects are obtained. That is, a difference in boiling point between palmitate etc. and oleate etc. in the second distillation in step (3) or (6) is sufficiently large although not as large as in the Aspect 1, and distillation separation is very effective. When a fat rich in OStO and a fat rich in POP are fractionated, not only a high purity fat composition may be obtained, but also the production cost may be further reduced by circularly reuse of each fractionated by-product to a raw material fat. In addition, when a fraction of unreacted fatty acid ester etc. obtained in each reaction system is circularly reused for raw material fatty acid ester etc. in the reaction system, the production cost may be further reduced.

In the USU-SUS combined reaction system, in another aspect (hereinafter referred to as the "Aspect 3") in the case where a USU-containing fat produced in the first reaction system is a fat rich in UStU (St is stearic acid), a fat (hereinafter referred to as "MOM fat") rich in saturated fatty acid with C4 to C14 at the 1,3 positions and rich in oleic acid at the 2-position is obtained by using high oleic fat for the raw material fat (c) in a second reaction step and using saturated fatty acid with C4 to C14 for the raw material fatty acid ester etc. (d). The MOM fat is fully hydrogenated to obtain a fat (hereinafter referred to as MStM fat) rich in stearic acid at the 2-position, and then the MStM fat is used for the raw material fat (a) in first reaction, and oleate etc. by-produced in a second reaction system is used for the raw material fatty acid ester etc. (b) to obtain fat rich in OStO. Here, by-produced saturated fatty acid ester etc. with C4 to C14 is used as the raw material fatty acid ester etc. (d) in the second reaction system. The conceptual diagram of Example 3 as an example of the Aspect 3 is shown in FIG. 4.

In the Aspect 3, details of high oleic fat of the raw material fat (c) and oleate etc. of the raw material fatty acid ester etc. (b) are the same as those of the Aspect 1.

In the Aspect 3, saturated fatty acid ester etc. with C4 to C14 is used for the raw material fatty acid ester etc. (d) in the second reaction system, and the content of saturated fatty acid with C4 to C14 in the raw material fatty acid ester etc. (d) is preferably 80% by weight or more, more preferably 90% by weight or more, further preferably 95% by weight or more, and most preferably 98% by weight or more.

MOM fat obtained in the second reaction system is hydrogenated to be MStM fat and used as the raw material fat (a). The raw material fat (a) preferably contains 10 to 70% by weight of saturated fatty acid with C4 to C14, and the lower limit thereof is more preferably 20% by weight or more, further preferably 30% by weight or more, and most preferably 40% by weight or more. The upper limit of saturated fatty acid with C4 to C14 is more preferably 60% by weight or less, and further preferably 55% by weight or less.

When saturated fatty acid with C4 to C14 in the constituent fatty acid of the raw material fat (a) of the present invention is contained in an amount of less than 10% by weight, the amount of saturated fatty acid ester etc. with C4 to C14 as by-product is small, and there is a problem that a sufficient amount may not be supplied as raw material fatty acid ester etc. in the second reaction system. When the content of saturated fatty acid with C4 to C14 exceeds 70% by weight, the content of St relatively decreases, so that a sufficient level of UStU fat production efficiency may not be obtained.

In the Aspect 3, in MStM fat used for the raw material fat (a), preferably 80% by weight or more, more preferably 90% by weight or more, further preferably 95% by weight or more, most preferably 98% by weight or more of saturated fatty acid with C4 to C14 in the constituent fatty acid are present at the 1,3-positions. When such a raw material fat is used, it is possible to easily perform separation by distillation by utilizing a difference between respective boiling points of saturated fatty acid ester etc. with C4 to C14 by-produced after interesterification and unreacted oleate etc. Saturated fatty acid ester etc. with C4 to C14 concentrated by separation may be effectively used as raw material fatty acid ester etc. in the second reaction system.

In the Aspect 3, a content ratio of saturated fatty acid with C4 to C14 to the S content is preferably 0.2 or more, more preferably 0.3 or more, further preferably 0.4 or more, and preferably 0.85 or less, more preferably 0.75 or less, and further preferably 0.85 or less, in the constituent fatty acid of the raw material fat (a). When this content ratio is less than the lower limit, the amount of by-produced saturated fatty acid ester etc. with C4 to C14 is small, and there is a problem that a sufficient amount may not be supplied as raw material fatty acid ester etc. in the second reaction system. When the content ratio exceeds the upper limit, the content of St relatively decreases, so that a sufficient level of UStU fat production efficiency may not be obtained.

In the Aspect 3, the following advantageous effects are obtained. That is, a difference in boiling point between saturated fatty acid ester etc. with C4 to C14 and oleate etc. in the second distillation in step (3) or (6) is sufficiently large as compared with the Aspect 1 and Aspect 2, and distillation separation is very effective. In this aspect, if conditions are set, it is possible to produce OStO-containing fat using only high oleic fat as almost the only raw material. If fractionated by-products of fat rich in OStO and fat rich in MOM produced in the reaction systems are circularly reused for raw material fat, or if a fraction of unreacted fatty acid etc. obtained in each reaction system is circularly reused for raw material fatty acid ester etc., the production cost is further reduced. Thus, it is possible to achieve an efficient, waste-free, ideal, and epoch-making process for producing OStO fat.

Also in the Aspect 1 and Aspect 2, in fat rich in BOB and fat rich in POP produced in the second reaction system, the component is hydrogenated by being concentrated or without being fractionated and concentrated to obtain a fat rich in stearic acid at the 2-position, so that this may be used as all or a part of the raw material fat (a) in step (1). In this case, as in the Aspect 3, UStU-containing fat may be produced by using only high oleic fat as a raw material such that by-product is not produced or is reduced, so that it is possible to achieve an efficient, waste-free, and ideal process for producing OStO fat.

In the USU-SUS combined reaction system, when a fat rich in USU produced in the first reaction system is a fat rich in UPU (P is palmitic acid), a UPU/USU ratio is preferably 0.5 or more, more preferably 0.7 or more, and further preferably 0.9 or more. One aspect (hereinafter referred to as the "Aspect 4") in this case is a process for producing OPO-containing fat by using a fat rich in PPP as the raw material fat (a) in the first reaction system and using oleate etc. for the raw material fatty acid ester etc. (b) and for producing POP-containing (P represents palmitic acid) fat by using high oleic fat for the raw material fat (c) in the second reaction system and using palmitate etc. for the raw material fatty acid ester etc. (d). Palmitate etc. by-produced in the first reaction system is used for the raw material fatty acid ester etc. (d) in the second reaction system, and oleate etc. by-produced in the second reaction system is used for the raw material fatty acid ester etc. (b) in the first reaction system. The conceptual diagram of Example 4 as an example of the Aspect 4 is shown in FIG. 5.

In the Aspect 4, the content of palmitic acid in the raw material fat (a) is preferably 60% by weight or more, more preferably 80% by weight or more, and most preferably 90% by weight or more. When palmitic acid in the constituent fatty acid of the raw material fat (a) is contained in an amount of less than 60% by weight, the amount of palmitate etc. as by-product is reduced, and there is a problem that a sufficient amount may not be supplied as raw material fatty acid ester etc. in the second reaction system. Moreover, it is not preferable because a sufficient level of OPO fat production efficiency may not be obtained. The raw material fat (a) is not particularly limited as long as the above-described requirements for the fatty acid composition are met. Examples of the raw material fat (a) include a palm fractionated high-melting point fraction and fully hydrogenated oil thereof, a fractionated high-melting point fraction of interesterified oil containing palm oil as a major raw material, and fully hydrogenated oil thereof, and tripalmitin fat. The raw material fat (a) is, most preferably palm fractionated high-melting point fraction or tripalmitin fat.

In the Aspect 4, in oleate etc. for the raw material fatty acid ester etc. (b), the content of oleic acid is preferably 70% by weight or more, and more preferably 75% by weight or more.

In the Aspect 4, as high oleic fat for the raw material fat (c), the content of oleic acid of fatty acid is preferably 70% by weight or more, more preferably 80% by weight or more, further preferably 90% by weight or more, and the content of linoleic acid is 20% by weight or less, preferably 15% by weight or less, more preferably 10% by weight or less, and most preferably 7% by weight or less. Examples of fat used for the raw material fat (c) include high oleic sunflower oil, high oleic safflower oil, high oleic rapeseed oil, olive oil, interesterified fat and fractionated fat of one or more fats selected therefrom, and fats which abundantly contain oleic acid and are subjected to interesterification with oleic acid or oleate to introduce oleic acid into triglyceride and thus to increase its content.

In the Aspect 4, in the second distillation in step (3) or (6), palmitate etc. and oleate etc. are separated. The distillation temperature in this case is preferably 120° C. or more, more preferably 140° C. or more, further preferably 150° C. or more, and most preferably 160° C. or more. In addition, the distillation temperature is preferably 220° C. or less, more preferably 210° C. or less, and further preferably 200° C. or less. The degree of vacuum is preferably 0.2 torr or more, more preferably 0.5 torr or more, and further preferably 1 torr or more. In addition, the degree of vacuum is preferably 10 torr or less, more preferably 7 torr or less, further preferably 5 torr or less, and the most preferably 3 torr or less. By the distillation, palmitate etc. is recovered to low-boiling point fraction, and oleate etc. is recovered to high-boiling point fraction.

In the Aspect 4, a fat rich in OPO is obtained in the first reaction system. In this case, the content of OPO is 30% by weight or more, preferably 40% by weight or more, more preferably 50% by weight or more, and most preferably 60% by weight or more. When fractionation is further performed, it is possible to obtain a fat composition having an improved OPO content in a fractionated low-melting point fraction, and a by-produced fractionated high-melting point fraction may be circularly used as a portion of the raw material fat (a) in step (1).

In the second reaction system of the Aspect 4, a fat rich in POP is produced. In this case, the content of POP is 30% by weight or more, preferably 40% by weight or more, more preferably 50% by weight or more, and most preferably 60% by weight or more. When fractionation is further performed, it is possible to obtain a fat composition having an improved POP content in a fractionated high-melting point fraction, and a by-produced fractionated low-melting point fraction may be circularly reused as a portion of the raw material fat (c) in step (4). In addition, a fraction of unreacted fatty acid ester etc. obtained in each reaction system may be circularly reused for raw material fatty acid ester etc. in the reaction system.

Hereinafter, examples of the present invention will be described to explain the present invention in more detail In the examples, both of % and part are weight basis.

The following Example 1 is an example of the Aspect 1, Example 2 is an example of the Aspect 2, Example 3 is an example of the Aspect 3, and Example 4 is an example of the Aspect 4, respectively.

Example 1

The conceptual diagram of Example 1 is shown in FIG. 2.
First Reaction System

A raw material mixture was prepared by mixing 30 parts of fully hydrogenated high erucic acid rapeseed oil (see FIG. 2-201) (99% by weight of S, 56% by weight of saturated fatty acid with C20 to C24, and 82.7% of saturated fatty acid with C20 to C24 at the 1,3-positions in the constituent fatty acid) as the raw material fat (a) and 70 parts of oleic acid ethyl ester (see FIG. 2-202) (81% by weight of oleic acid ethyl ester content) as the raw material fatty acid ester etc. (b). The mixture was bleached and dehydrated by a known method, and then subjected to interesterification using 1,3-position-specific lipase. The interesterification was performed by a batch reaction with 90 ppm of water content in the raw material mixture, 24 hours of reaction time, 53° C. of reaction temperature, and 1% of immobilized lipase relative to the raw material mixture.

After the reaction, the obtained reaction product was separated into a triglyceride fraction and a fatty acid ethyl ester fraction by the distillation. Conditions for the distillation were 245 to 250° C. of temperature and 0.5 to 1.0 torr of the degree of vacuum. The USU content of the obtained triglyceride fraction (see FIG. 2-203) was 45% by weight. The triglyceride fraction was further subjected to solvent fractionation using N-hexane to obtain a fat composition (OStO fat) containing 87% by weight of USU, 58% by weight of OStO, and 1% by weight of OBO as a low-melting point fraction. In addition, high-melting point fraction fat was obtained as a by-product. This high-melting point fraction fat was circularly reused as a portion of the raw material mixture. The fatty acid ethyl ester fraction obtained by the distillation was separated into the low-boiling point fraction and the high-boiling point fraction in the subsequent rectification step. Conditions for the rectification were 238 to 241° C. of temperature and 1.1 to 1.3 torr of the degree of vacuum. The obtained low-boiling point fraction (see FIG. 2-204) contained 83% by weight of oleic acid ethyl ester. The low-boiling point fraction had a quality almost equivalent to the raw material fatty acid ester etc. (b) containing 81% by weight of ethyl oleate and was substituted as a portion of the raw material fatty acid ester etc. (b) for circular reuse to the next interesterification. The obtained high-boiling point fraction (see FIG. 2-205) was by-product fatty acid ester etc. derived from the 1,3-positions of the raw material fat, contained 83% by weight of behenic acid ethyl ester, had a quality almost equivalent to the raw material fatty acid ester etc. (d) in the second reaction system, and was used as a portion of the (d) (see FIG. 2-206).

Second Reaction System

A raw material mixture was prepared by mixing 30 parts of high oleic sunflower oil (see FIG. 2-207) (88% by weight of oleic acid content and 91% by weight of U content in the constituent fatty acid) as the raw material fat (c) and 70 parts of behenic acid ethyl ester (see FIG. 2-208) (91% by weight of behenic acid ethyl ester content and 99% by weight of S content) as the raw material fatty acid ester etc. (b). The mixture was bleached and dehydrated by a known method, and then subjected to interesterification using 1,3-position-specific lipase. The interesterification was performed by a batch reaction with 90 ppm of water content in the raw material mixture, 24 hours of reaction time, 53° C. of reaction temperature, and 1% of immobilized lipase relative to the raw material mixture.

After the reaction, the obtained reaction product was separated into a triglyceride fraction and a fatty acid ethyl ester fraction by the distillation. Conditions for the distillation were 245 to 250° C. of temperature and 0.5 to 1.0 torr of the degree of vacuum. The SUS content of the obtained triglyceride fraction (see FIG. 2-209) was 45% by weight. The triglyceride fraction was further subjected to solvent fractionation using N-hexane to obtain a fat composition (BOB fat) containing 87% by weight of SUS and 66% by weight of BOB as a high-melting point fraction. In addition, a low-melting point fraction was obtained as a by-product. This low-melting point fraction was circularly reused as a portion of the raw material mixture. The fatty acid ethyl ester fraction obtained by the distillation was separated into the low-boiling point fraction and the high-boiling point fraction in the subsequent rectification step. Conditions for the rectification were 238 to 241° C. of temperature and 1.1 to 1.3 torr of the degree of vacuum. The obtained low-boiling point fraction (see FIG. 2-211) was by-product fatty acid ester etc. derived from the 1,3-positions of the raw material fat, contained 83% by weight of oleic acid ethyl ester, had a quality almost equivalent to the raw material fatty acid ester etc. (b) containing 81% by weight of ethyl oleate in the first reaction system, and was substituted as a portion of the (b) for use (see FIG. 2-212). The obtained high-boiling point fraction (see FIG. 2-210) contained 83% by weight of behenic acid ethyl ester, had a quality almost equivalent to the raw material fatty acid ester etc. (d), and was circularly reused as a portion of the (d).

That is, behenic acid ester etc. by-produced in the first reaction system was used for the raw material fatty acid ester etc. in the second reaction system, and oleic acid by-produced in the second reaction system was used for the raw material fatty acid ester etc. in the first reaction system, so that OStO fat and BOB fat were produced efficiently. Moreover, when by-product fat produced by fractionation of a fat composition and unreacted fatty acid esters etc. were circularly reused as raw materials, OStO fat and BOB fat was produced more efficiently.

In addition, the obtained BOB fat was fully hydrogenated and thereafter used for the raw material fat (a) in step (1). This is an efficient, waste-free, and ideal process for producing OStO fat, which enables to produce OStO fat substantially without generating by-product by using only high oleic fat as a raw material.

Example 2

The conceptual diagram of Example 2 is shown in FIG. 3.
First Reaction System

A raw material mixture was prepared by mixing 30 parts of fully hydrogenated oil of palm mid fraction (see FIG. 3-301) (99% by weight of S content, 57% by weight of palmitic acid content, and 82.7% of palmitic acid content at the 1,3-positions in the constituent fatty acid) as the raw material fat (a) and 70 parts of oleic acid ethyl ester (see FIG. 3-302) (81% by weight of oleic acid ethyl ester content) as the raw material fatty acid ester etc. (b). The mixture was bleached and dehydrated by a known method, and then subjected to interesterification using 1,3-position-specific lipase. The interesterification was performed by a batch reaction with 90 ppm of water content in the raw material mixture, 24 hours of reaction time, 53° C. of reaction temperature, and 1% of immobilized lipase relative to the raw material mixture.

After the reaction, the obtained reaction product was separated into a triglyceride fraction and a fatty acid ethyl ester fraction by the distillation. Conditions for the distillation were 235 to 240° C. of temperature and 0.5 to 1.0 torr of the degree of vacuum. The USU content of the obtained triglyceride fraction (see FIG. 3-303) was 43% by weight. The triglyceride fraction was further subjected to solvent fractionation using N-hexane to obtain a fat composition (OStO fat) containing 87% by weight of USU and 67% by weight of OStO as a low-melting point fraction. In addition, a high-melting point fraction was obtained as a by-product. This high-melting point fraction was circularly reused as a portion of the raw material mixture. The fatty acid ethyl ester fraction obtained by the distillation was separated into the low-boiling point fraction and the high-boiling point fraction in the subsequent rectification step. Conditions for the rectification were 218 to 221° C. of temperature and 1.1 to 1.3 torr of the degree of vacuum. The obtained high-boiling point fraction (see FIG. 3-304) contained 83% by weight of oleic acid ethyl ester. The high-boiling point fraction had a quality almost equivalent to the raw material fatty acid ester etc. (b) containing 81% by weight of ethyl oleate and was substituted as a portion of the raw material fatty acid ester etc. (b) for circular reuse to the next interesterification. The obtained low-boiling point fraction (see FIG. 3-305) was by-product fatty acid ester etc. derived from the 1,3-positions of the raw material fat, contained 88% by weight of palmitic acid ethyl ester, had a quality almost equivalent to the raw material fatty acid ester etc. (d) in the second reaction system, and was used as a portion of the (d) (see FIG. 3-306).

Second Reaction System

A raw material mixture was prepared by mixing 30 parts of high oleic sunflower oil (see FIG. 3-307) (88% by weight of oleic acid content and 91% by weight of U content in the constituent fatty acid) as the raw material fat (c) and 70 parts of palmitic acid ethyl ester (see FIG. 3-308) (88% by weight of palmitic acid ethyl ester content and 93% by weight of S content) as the raw material fatty acid ester etc. (d). The mixture was bleached and dehydrated by a known method, and then subjected to interesterification using 1,3-position-specific lipase. The interesterification was performed by a batch reaction with 90 ppm of water content in the raw material mixture, 24 hours of reaction time, 43° C. of reaction temperature, and 1% of immobilized lipase relative to the raw material mixture.

After the reaction, the obtained reaction product was separated into a triglyceride fraction and a fatty acid ethyl ester fraction by the distillation. Conditions for the distillation were 235 to 240° C. of temperature and 0.5 to 1.0 torr of the degree of vacuum. The SUS content of the obtained triglyceride fraction (see FIG. 3-309) was 48% by weight. The triglyceride fraction was further subjected to solvent fractionation using N-hexane to obtain a fat composition (POP fat) containing 87% by weight of SUS and 77% by weight of POP as a high-melting point fraction. In addition, a low-melting point fraction was obtained as a by-product. This low-melting point fraction was circularly reused as a portion of the raw material mixture. The fatty acid ethyl ester fraction obtained by the distillation was separated into the low-boiling point fraction and the high-boiling point fraction in the subsequent rectification step. Conditions for the rectification were 218 to 221° C. of temperature and 1.1 to 1.3 torr of the degree of vacuum. The obtained low-boiling point fraction (see FIG. 3-310) contained 88% by weight of palmitic acid ethyl ester, had a quality almost equivalent to the raw material fatty acid ester etc. (d), and was circularly reused as a portion of the (d). The obtained high-boiling point fraction (see FIG. 3-311) was by-product fatty acid ester etc. derived from the 1,3-positions of the raw material fat, contained 83% by weight of oleic acid ethyl ester, had a quality almost equivalent to the raw material fatty acid ester etc. (b) containing 81% by weight of ethyl oleate in the first reaction system, and was used as a portion of the (b) (see FIG. 3-312).

That is, palmitate etc. by-produced in the first reaction system was used for the raw material fatty acid ester etc. in the second reaction system, and oleate etc. by-produced in the second reaction system was used for the raw material fatty acid ester etc. in the first reaction system, so that OStO fat and POP fat were produced efficiently. Moreover, when by-product fat produced by fractionation of a fat composition and unreacted fatty acid esters etc. were circularly reused as raw materials, OStO fat and POP fat were produced more efficiently.

In addition, the obtained POP fat was fully hydrogenated and thereafter used for the raw material fat (a) in step (1). This is an efficient, waste-free, and ideal process for producing OStO fat, which enables to produce OStO fat substantially without generating by-product by using only high oleic fat as a raw material.

Example 3

The conceptual diagram of Example 3 is shown in FIG. 4.
Second Reaction System
A raw material mixture was prepared by mixing 30 parts of high oleic sunflower oil (see FIG. 4-407) (88% by weight of oleic acid content and 91% by weight of U content in the constituent fatty acid) as the raw material fat (c) and 70 parts of caprylic acid ethyl ester (see FIG. 4-408) (hereinafter referred to as "C8 ethyl ester", 99% by weight of C8 ethyl ester content) as the raw material fatty acid ester etc. (d). The mixture was bleached and dehydrated by a known method, and then subjected to interesterification using 1,3-position-specific lipase. The interesterification was performed by a batch reaction with 90 ppm of water content in the raw material mixture, 24 hours of reaction time, 43° C. of reaction temperature, and 1% of immobilized lipase relative to the raw material mixture.

After the reaction, the obtained reaction product was separated into a triglyceride fraction and a fatty acid ethyl ester fraction by the distillation. Conditions for the distillation were 235 to 240° C. of temperature and 0.5 to 1.0 torr of the degree of vacuum. The SUS content of the obtained triglyceride fraction (see FIG. 4-409) was 73% by weight. The triglyceride fraction was further subjected to solvent fractionation using N-hexane to obtain a fat composition (C8O08 fat) containing 95% by weight of SUS and 92% by weight of C8O08 as a high-melting point fraction. This high-melting point fraction was subjected to fully hydrogenation by a known method to obtain a fat rich in C8StC8 (see FIG. 4-413). The fatty acid ethyl ester fraction obtained by the distillation was separated into the low-boiling point fraction and the high-boiling point fraction in the subsequent rectification step. Conditions for the rectification were 90 to 130° C. of temperature and 1.1 to 1.3 torr of the degree of vacuum. The obtained high-boiling point fraction (see FIG. 4-411) was by-product fatty acid ester etc. derived from the 1,3-positions of the raw material fat, contained 86% by weight of oleic acid ethyl ester, had a quality almost equivalent to the raw material fatty acid ester etc. (b) in the first reaction system, and was used as a portion of the (b) (see FIG. 4-412). The obtained low-boiling point fraction contained 99% by weight of C8 ethyl ester. The low-boiling point fraction had a quality almost equivalent to the raw material fatty acid ester etc. (d) and was substituted as a portion of the raw material fatty acid ester etc. (d) for circular reuse to the next interesterification. The low-melting point fraction obtained as a by-product in the solvent fractionation was circularly reused as a portion of the raw material mixture.

First Reaction System A raw material mixture was prepared by mixing 30 parts of fat rich in C8StC8 (see FIG. 4-401) (99% by weight of S content, 49% by weight of saturated fatty acid content of C8, and 51% by weight of St content in the constituent fatty acid) obtained in the second reaction system as the raw material fat (a) and 70 parts of oleic acid ethyl ester (see FIG. 4-402) (87% by weight of oleic acid ethyl ester content) as the raw material fatty acid ester etc. (b). The mixture was bleached and dehydrated by a known method, and then subjected to interesterification using 1,3-position-specific lipase. The interesterification was performed by a batch reaction with 90 ppm of water content in the raw material mixture, 24 hours of reaction time, 53° C. of reaction temperature, and 1% of immobilized lipase relative to the raw material mixture.

After the reaction, the obtained reaction product was separated into a triglyceride fraction and a fatty acid ethyl ester fraction by the distillation. Conditions for the distillation were 235 to 240° C. of temperature and 0.5 to 1.0 torr of the degree of vacuum. The USU content of the obtained triglyceride fraction (see FIG. 4-403) was 43% by weight. The triglyceride fraction was further subjected to solvent fractionation using N-hexane to obtain a fat composition (OStO fat) containing 87% by weight of USU and 80% by weight of OStO as a low-melting point fraction. The fatty acid ethyl ester fraction obtained by the distillation was separated into the low-boiling point fraction and the high-boiling point fraction in the subsequent rectification step. Conditions for the rectification were 90 to 130° C. of temperature and 1.1 to 1.3 torr of the degree of vacuum. The obtained high-boiling point fraction (see FIG. 4-404) contained 86% by weight of oleic acid ethyl ester. The high-boiling point fraction had a quality almost equivalent to the raw material fatty acid ester etc. (b) containing 87% by weight of ethyl oleate and was substituted as a portion of the (b) for circular reuse to the next interesterification. The obtained low-boiling point fraction (see FIG. 4-405) was by-product fatty acid ester etc. derived from the 1,3-positions of the raw material fat, contained 99% by weight of C8 ethyl ester, had a quality almost equivalent to the raw material fatty acid ester etc. (d) in the second reaction system, and was used as a portion of the (d) (see FIG. 4-406). The high-melting point fraction obtained as a by-product in the solvent fractionation was circularly reused as a portion of the raw material mixture.

That is, fat rich in C8OC8 fat obtained in the second reaction system was fractionated and then fully hydrogenated to obtain fat rich in C8StC8, the fat rich in C8StC8 was used as raw material fat in the first reaction system, oleate etc. derived from the 1,3-positions of raw material fat, which was by-produced in the second reaction system, was used for raw material fatty acid ester etc. in the first reaction system, C8 ester by-produced in the first reaction system was used for raw material fatty acid ester etc. in the second reaction system, and, in addition, by-product fat produced by fractionation of a fat composition and unreacted fatty acid esters etc. were circularly reused as raw materials, so that OStO fat was efficiently produced using high oleic sunflower oil as the only raw material in a state in which C8 ester etc. and oleate etc. were almost completely recycled.

Example 4

The conceptual diagram of Example 4 is shown in FIG. 5.
First Reaction System

A raw material mixture was prepared by mixing 30 parts of palm fractionated high-melting point fraction (see FIG. 5-501) (88% by weight of S content and 83% by weight of palmitic acid content in the constituent fatty acid) as the raw material fat (a) and 70 parts of oleic acid ethyl ester (see FIG. 5-502) (86% by weight of oleic acid ethyl ester content) as the raw material fatty acid ester etc. (b). The mixture was bleached and dehydrated by a known method, and then subjected to interesterification using 1,3-position-specific lipase. The interesterification was performed by a batch reaction with 90 ppm of water content in the raw material mixture, 24 hours of reaction time, 53° C. of reaction temperature, and 1% of immobilized lipase relative to the raw material mixture.

After the reaction, the obtained reaction product was separated into a triglyceride fraction and a fatty acid ethyl ester fraction by the distillation. Conditions for the distillation were 235 to 240° C. of temperature and 0.5 to 1.0 torr of the degree of vacuum. The USU content of the obtained triglyceride fraction (see FIG. 5-503) was 38% by weight. The triglyceride fraction was further subjected to solvent fractionation using N-hexane to obtain a fat composition (OPO fat) containing 60% by weight of USU and 52% by weight of OPO as a low-melting point fraction.

In addition, a high-melting point fraction was obtained as a by-product. This high-melting point fraction was circularly reused as a portion of the raw material mixture. The fatty acid ethyl ester fraction obtained by the distillation was separated into the low-boiling point fraction and the high-boiling point fraction in the subsequent rectification step. Conditions for the rectification were 218 to 221° C. of temperature and 1.1 to 1.3 torr of the degree of vacuum. The obtained high-boiling point fraction (see FIG. 5-504) contained 83% by weight of oleic acid ethyl ester. The high-boiling point fraction had a quality almost equivalent to the raw material fatty acid ester etc. (b) containing 81% by weight of ethyl oleate and was substituted as a portion of the raw material fatty acid ester etc. (b) for circular reuse to the next interesterification. The obtained low-boiling point fraction (see FIG. 5-505) was by-product fatty acid ester etc. derived from the 1,3-positions of the raw material fat, contained 88% by weight of palmitic acid ethyl ester, had a quality almost equivalent to the raw material fatty acid ester etc. (d) in the second reaction system, and was used as a portion of the (d) (see FIG. 5-506).

Second Reaction System

A raw material mixture was prepared by mixing 30 parts of high oleic sunflower oil (see FIG. 5-507) (88% by weight of oleic acid content and 91% by weight of U content in the constituent fatty acid) as the raw material fat (c) and 70 parts of palmitic acid ethyl ester (see FIG. 5-508) (88% by weight of palmitic acid ethyl ester content and 93% by weight of S content) as the raw material fatty acid ester etc. (d). The mixture was bleached and dehydrated by a known method, and then subjected to interesterification using 1,3-position-specific lipase. The interesterification was performed by a batch reaction with 90 ppm of water content in the raw material mixture, 24 hours of reaction time, 43° C. of reaction temperature, and 1% of immobilized lipase relative to the raw material mixture.

After the reaction, the obtained reaction product was separated into a triglyceride fraction and a fatty acid ethyl ester fraction by the distillation. Conditions for the distillation were 235 to 240° C. of temperature and 0.5 to 1.0 torr of the degree of vacuum. The SUS content of the obtained triglyceride fraction (see FIG. 5-509) was 48% by weight. The triglyceride fraction was further subjected to solvent fractionation using N-hexane to obtain a fat composition (POP fat) containing 87% by weight of SUS and 77% by weight of POP as a high-melting point fraction. In addition, a low-melting point fraction was obtained as a by-product. This low-melting point fraction was circularly reused as a portion of the raw material mixture. The fatty acid ethyl ester fraction obtained by the distillation was separated into the low-boiling point fraction and the high-boiling point fraction in the subsequent rectification step. Conditions for the rectification were 218 to 221° C. of temperature and 1.1 to 1.3 torr of the degree of vacuum. The obtained low-boiling point fraction (see FIG. 5-510) contained 88% by weight of palmitic acid ethyl ester, had a quality almost equivalent to the raw material fatty acid ester etc. (d), and was circularly reused as a portion of the (d). The obtained high-boiling point fraction (see FIG. 5-511) was by-product fatty acid ester etc. derived from the 1,3-positions of the raw material fat, contained 83% by weight of oleic acid ethyl ester, had a quality almost equivalent to the raw material fatty acid ester etc. (b) containing 81% by weight of ethyl oleate in the first reaction system, and was used as a portion of the (b) (see FIG. 5-512).

That is, palmitate etc. by-produced in the first reaction system was used for the raw material fatty acid ester etc. in the second reaction system, and palmitate etc. by-produced in the second reaction system was used for the raw material fatty acid ester etc. in the first reaction system, so that OPO fat and POP fat were produced efficiently. Moreover, when by-product fat produced by fractionation of a fat composition and unreacted fatty acid esters etc. were circularly reused as raw materials, OPO fat and POP fat were produced more efficiently.

Example 5

First Reaction System

A raw material mixture was prepared by mixing 30 parts of fully hydrogenated rapeseed oil (99% by weight of S content and 2.2% by weight of the content of saturated fatty acid with C20 to C24 in the constituent fatty acid) as the raw material fat (a) and 70 parts of oleic acid ethyl ester (81% by weight of oleic acid ethyl ester content) as the raw material fatty acid ester etc. (b). The mixture was bleached and dehydrated by a known method, and then subjected to interesterification using 1,3-position-specific lipase. The interesterification was performed by a batch reaction with 90 ppm of water content in the raw material mixture, 24 hours of reaction time, 53° C. of reaction temperature, and 1% of immobilized lipase relative to the raw material mixture.

After the reaction, the obtained reaction product was separated into a triglyceride fraction and a fatty acid ethyl ester fraction by the distillation. Conditions for the distillation were 235 to 240° C. of temperature and 0.5 to 1.0 torr of the degree of vacuum. The USU content of the obtained triglyceride fraction was 43% by weight. The triglyceride fraction was further subjected to solvent fractionation using N-hexane to obtain a fat composition (OStO fat) containing 87% by weight of USU, 67% by weight of OStO, and 0% by weight of OBO as a low-melting point fraction. In addition, a high-melting point fraction was obtained as a by-product. This high-melting point fraction was circularly reused as a portion of the raw material mixture. The fatty acid ethyl ester fraction obtained by the distillation was cooled at 20° C., and a fraction of fatty acid ester etc. containing 84% by weight of S as a high-melting point fraction and a low-melting point fraction containing 96% by weight of oleic acid ethyl ester were obtained by filtration. Among them, the low-melting point fraction had a quality almost equivalent to the raw material fatty acid ester etc. (b) containing 81% by weight of ethyl oleate and was substituted as a portion of the raw material fatty acid ester etc. (b) for reuse to the next interesterification. That is, the production cost of OStO fat was reduced by circularly reusing unreacted ethyl oleate. The obtained high-melting point fraction had a quality almost equivalent to the raw material fatty acid ester etc. (d) in the second reaction system and was substituted as a portion of the (d) for use.

Second Reaction System

A raw material mixture was prepared by mixing 30 parts of high oleic sunflower oil (88% by weight of oleic acid content and 91% by weight of U content in the constituent fatty acid) as the raw material fat (c) and 70 parts of stearic acid ethyl ester (92% by weight of stearic acid ethyl ester content and 99% by weight of S content) as the raw material fatty acid ester etc. (d). The mixture was bleached and dehydrated by a known method, and then subjected to interesterification using 1,3-position-specific lipase. The interesterification was performed by a batch reaction with 90 ppm of water content in the raw material mixture, 24 hours of reaction time, 43° C. of reaction temperature, and 1% of immobilized lipase relative to the raw material mixture.

After the reaction, the obtained reaction product was separated into a triglyceride fraction and a fatty acid ethyl ester fraction by the distillation. Conditions for the distillation were 235 to 240° C. of temperature and 0.5 to 1.0 torr of the degree of vacuum. The SUS content of the obtained triglyceride fraction was 45% by weight. The triglyceride fraction was further subjected to solvent fractionation using N-hexane to obtain a fat composition (StOSt fat) containing 87% by weight of SUS and 77% by weight of StOSt as a high-melting point fraction. In addition, a low-melting point fraction was obtained as a by-product. This low-melting point fraction was circularly reused as a portion of the raw material mixture. The fatty acid ethyl ester fraction obtained by the distillation was cooled at 20° C., and a fraction of fatty acid ester etc. containing 92% by weight of S as a high-melting point fraction and a low-melting point fraction containing 89% by weight of oleic acid ethyl ester were obtained by filtration. Among them, the high-melting point fraction had a quality almost equivalent to the raw material fatty acid ester etc. (d) containing 99% by weight of S and was substituted as a portion of the raw material fatty acid ester etc. (d) for circular reuse to the next interesterification. The obtained low-melting point fraction had a quality almost equivalent to the raw material fatty acid ester etc. (d) in the second reaction system and was substituted as a portion of the (d) for use.

That is, stearate etc. by-produced in the first reaction system was used for the raw material fatty acid ester etc. in the second reaction system, and oleate etc. by-produced in the second reaction system was used for the raw material fatty acid ester etc. in the first reaction system, so that OStO fat and StOSt fat were produced efficiently. Moreover, when by-product fat produced by fractionation of a fat composition and unreacted fatty acid esters etc. were circularly reused as raw materials, OStO fat and StOSt fat were produced more efficiently. Among Examples 1, 2, 3 and 5, Examples 1, 2 and 3 were particularly excellent as a process for producing OStO fat efficiently.

EXPLANATION OF REFERENCE NUMERALS

FIG. 1-101 Fat rich in SSS
FIG. 1-102 Fatty acid ester etc. containing U as major component
FIG. 1-103 USU-containing fat composition
FIG. 1-104 Fatty acid ester etc. containing U as major component
FIG. 1-105 Fatty acid ester etc. containing S as major component
FIG. 1-106 Used for raw material fatty acid ester etc. (d) in second reaction system
FIG. 1-107 Raw material fat (c) as fat rich in UUU
FIG. 1-108 Raw material fatty acid ester etc. (d) containing S as major component
FIG. 1-109 SUS-containing fat composition
FIG. 1-110 Fatty acid ester etc. containing S as major component
FIG. 1-111 Fatty acid ester etc. containing U as major component
FIG. 1-112 Used for raw material fatty acid ester etc. (b) in first reaction system
FIG. 2-201 Fully hydrogenated high erucic acid rapeseed oil
FIG. 2-202 Oleic acid ethyl ester
FIG. 2-203 OStO-containing fat composition
FIG. 2-204 Oleic acid ethyl ester
FIG. 2-205 Behenic acid ethyl ester
FIG. 2-206 Used for behenic acid ethyl ester in second reaction system
FIG. 2-207 High oleic sunflower oil
FIG. 2-208 Behenic acid ethyl ester
FIG. 2-209 BOB-containing fat composition
FIG. 2-210 Behenic acid ethyl ester
FIG. 2-211 Oleic acid ethyl ester
FIG. 2-212 Used for oleic acid ethyl ester in first reaction system
FIG. 3-301 Fully hydrogenated oil of palm mid fraction
FIG. 3-302 Oleic acid ethyl ester
FIG. 3-303 OStO-containing fat composition
FIG. 3-304 Oleic acid ethyl ester
FIG. 3-305 Palmitic acid ethyl ester
FIG. 3-306 Used for palmitic acid ethyl ester in second reaction system
FIG. 3-307 High oleic sunflower oil
FIG. 3-308 Palmitic acid ethyl ester
FIG. 3-309 POP-containing fat composition
FIG. 3-310 Palmitic acid ethyl ester
FIG. 3-311 Oleic acid ethyl ester
FIG. 3-312 Used for oleic acid ethyl ester in first reaction system
FIG. 4-401 C8StC8 fat
FIG. 4-402 Oleic acid ethyl ester
FIG. 4-403 OStO-containing fat composition
FIG. 4-404 Oleic acid ethyl ester
FIG. 4-405 C8 ethyl ester
FIG. 4-406 Used for C8 ethyl ester in second reaction system FIG. 4-407 High oleic sunflower oil
FIG. 4-408 C8 ethyl ester
FIG. 4-409 C8OC8-containing fat composition
FIG. 4-410 C8 ethyl ester
FIG. 4-411 Oleic acid ethyl ester
FIG. 4-412 Used for oleic acid ethyl ester in first reaction system
FIG. 4-413 Used for C8StC8 fat in first reaction system after fractionation and hardening
FIG. 5-501 Palm fractionated high-melting point fraction
FIG. 5-502 Oleic acid ethyl ester
FIG. 5-503 OPO-containing fat composition
FIG. 5-504 Oleic acid ethyl ester
FIG. 5-505 Palmitic acid ethyl ester
FIG. 5-506 Used for palmitic acid ethyl ester in second reaction system
FIG. 5-507 High oleic sunflower oil
FIG. 5-508 Palmitic acid ethyl ester
FIG. 5-509 POP-containing fat composition
FIG. 5-510 Palmitic acid ethyl ester
FIG. 5-511 Oleic acid ethyl ester
FIG. 5-512 Used for oleic acid ethyl ester in first reaction system

The invention claimed is:

1. A process for producing a plurality of fat compositions by a combined reaction system, wherein the combined reaction system comprises a first reaction system which produces a fat composition rich in USU and a second reaction system which produces a fat composition rich in SUS, the first reaction system comprises the following steps (1) to (3), the second reaction system comprises the following steps (4) to (6), wherein a fraction obtained in step (6) is used for a part or all of raw material fatty acid or lower alcohol ester thereof (b) in step (1), and wherein a fraction obtained in step (3) is used for a part or all of raw material fatty acid or lower alcohol ester thereof (d) in step (4), wherein S represents saturated fatty acid with C4 to C24, U represents unsaturated fatty acid with C18, USU represents triglyceride in which fatty acids at 1,3-positions are U and fatty acid at 2-position is S, and SUS represents triglyceride in which fatty acids at 1,3-positions are S and fatty acid at 2-position is U, and wherein steps (1) to (6) are as follows:
(1) a step of mixing raw material fat (a) comprising 80% by weight or more of S in the constituent fatty acid and raw material fatty acid or lower alcohol ester thereof (b) comprising U as a major component;
(2) a step of subjecting the raw material mixture obtained in step (1) to interesterification using 1,3-position-specific lipase;
(3) a step of separating a fraction of fatty acid or lower alcohol ester thereof, which is liberated derived from the 1,3-positions of the raw material fat (a), by distillation from a reaction product obtained in step (2);
(4) a step of mixing raw material fat (c) comprising 50% by weight or more of U in the constituent fatty acid and raw material fatty acid or lower alcohol ester thereof (d) comprising S as a major component;
(5) a step of subjecting the raw material mixture obtained in step (4) to interesterification using 1,3-position-specific lipase; and
(6) a step of separating a fraction of fatty acid or a lower alcohol ester thereof, which is liberated derived from the 1,3-positions of the raw material fat (c), by distillation from a reaction product obtained in step (5).

2. The process for producing a plurality of fat compositions according to claim 1, wherein in step (3), a fat composition comprising 30% by weight or more of USU and a fraction of unreacted fatty acid or lower alcohol ester thereof are separated from the reaction product.

3. The process for producing a plurality of fat compositions according to claim 1, wherein in step (6), a fat composition comprising 30% by weight or more of SUS and a fraction of unreacted fatty acid or a lower alcohol ester thereof are separated from the reaction product.

4. The process for producing a plurality of fat compositions according to claim 1, wherein the USU comprises stearic acid (St) as a major component of fatty acid at 2-position, and has 0.5 or more of UStU/USU ratio.

5. The process for producing a plurality of fat compositions according to claim 4, wherein the raw material fat (a) comprises 10 to 70% by weight of saturated fatty acid with C20 to C24 in the constituent fatty acid.

6. The process for producing a plurality of fat compositions according to claim 5, wherein a fully hydrogenated oil of high erucic rapeseed oil is used for a part or all of the raw material fat (a), wherein oleic acid or lower alcohol ester thereof is used for the raw material fatty acid or lower alcohol ester thereof (b), wherein high oleic fat is used for a part or all of the raw material fat (c), and wherein behenic acid or lower alcohol ester thereof is used for the raw material fatty acid or lower alcohol ester thereof (d).

7. The process for producing a plurality of fat compositions according to claim 4, wherein the raw material fat (a) comprises 10 to 70% by weight of saturated fatty acid with C4 to C16 in the constituent fatty acid.

8. The process for producing a plurality of fat compositions according to claim 7, wherein a fully hydrogenated oil of palm mid fraction is used for a part or all of the raw material fat (a), wherein oleic acid or lower alcohol ester thereof is used for the raw material fatty acid or lower alcohol ester thereof (b), wherein high oleic fat is used for a part or all of the raw material fat (c), and wherein palmitic acid or lower alcohol ester thereof is used for the raw material fatty acid or lower alcohol ester thereof (d).

9. The process for producing a plurality of fat compositions according to claim 4, wherein a triglyceride fraction obtained in step (6) is fully hydrogenated and used for a part or all of the raw material fat (a) in step (1).

10. The process for producing a plurality of fat compositions according to claim 1, wherein the USU contains palmitic acid (P) as a major component of fatty acid at 2-position, and has 0.5 or more of UPU/USU ratio.

11. The process for producing a plurality of fat compositions according to claim 10, wherein the raw material fat (a) comprises 60% by weight or more of palmitic acid in the constituent fatty acid.

12. The process for producing a plurality of fat compositions according to claim 11, wherein a fat rich in tripalmitin is used for a part or all of the raw material fat (a), wherein oleic acid or lower alcohol ester thereof is used for the raw material fatty acid or lower alcohol ester thereof (b), wherein high oleic fat is used for a part or all of the raw material fat (c), and wherein palmitic acid or lower alcohol ester thereof is used for the raw material fatty acid or lower alcohol ester thereof (d).

13. The process for producing a plurality of fat compositions according to claim 12, wherein the raw material fat (c) comprises 70% by weight or more of oleic acid and 20% by weight or less of linoleic acid.

14. The process for producing a plurality of fat compositions according to claim 13, wherein the raw material fat (c) is an interesterified fat or a fractionated fat of one or more fats selected from the group consisting of high oleic sunflower oil, high oleic safflower oil, high oleic rapeseed oil and olive oil.

15. The process for producing a plurality of fat compositions according to claim 6, wherein steps (3) and (6) comprise a first and a second distillation, wherein the first distillation separates the interesterified mixture to a triglyceride fraction and a fraction of fatty acid ester, and wherein the second distillation separates the fraction of fatty acid ester to a fraction of by-product fatty acid ester derived from the 1,3-positions of the raw material fat and a fraction of other fatty acid ester.

16. The process for producing a plurality of fat compositions according to claim 15, wherein a temperature of the first distillation is 180° C. or more and 280° C. or less, and wherein a degree of vacuum of the first distillation is 0.2 torr or more and 10 torr or less, wherein a temperature of the second distillation is 170° C. or more and 270° C. or less, and wherein a degree of vacuum of the second distillation is 0.2 torr or more and 10 torr or less.

17. The process for producing a plurality of fat compositions according to claim 8, wherein steps (3) and (6) comprise a first and a second distillation, wherein the first distillation separates the interesterified mixture to a triglyceride fraction and a fraction of fatty acid ester, and wherein the second distillation separates the fraction of fatty acid ester to a fraction of by-product fatty acid ester derived from the 1,3-positions of the raw material fat and a fraction of other fatty acid ester.

18. The process for producing a plurality of fat compositions according to claim 17, wherein a temperature of the first distillation is 180° C. or more and 280° C. or less, and wherein a degree of vacuum of the first distillation is 0.2 torr or more and 10 torr or less, wherein a temperature of the second distillation is 120° C. or more and 220° C. or less, and wherein a degree of vacuum of the second distillation is 0.2 torr or more and 10 torr or less.

19. The process for producing a plurality of fat compositions according to claim 14, wherein steps (3) and (6) comprise a first and a second distillation, wherein the first distillation separates the interesterified mixture to a triglyceride fraction and a fraction of fatty acid ester, and wherein the second distillation separates the fraction of fatty acid ester to a fraction of by-product fatty acid ester derived from the 1,3-positions of the raw material fat and a fraction of other fatty acid ester.

20. The process for producing a plurality of fat compositions according to claim 19, wherein a temperature of the first distillation is 180° C. or more and 280° C. or less, and wherein a degree of vacuum of the first distillation is 0.2 torr or more and 10 torr or less, wherein a temperature of the second distillation is 120° C. or more and 220° C. or less, and wherein a degree of vacuum of the second distillation is 0.2 torr or more and 10 torr or less.

21. The process for producing a plurality of fat compositions according to claim 14, wherein steps (3) and (6) comprise one distillation which separates the interesterified mixture to a triglyceride fraction, a fraction of by-product fatty acid ester derived from the 1,3-positions of the raw material fat and a fraction of other fatty acid ester.

* * * * *